United States Patent
Eidenschink et al.

(10) Patent No.: US 7,225,518 B2
(45) Date of Patent: Jun. 5, 2007

(54) APPARATUS FOR CRIMPING A STENT ASSEMBLY

(75) Inventors: Tracee Eidenschink, Wayzata, MN (US); Jan Weber, Maple Grove, MN (US); Karl A. Jagger, Maple Grove, MN (US); Terry V. Brown, Fridley, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 254 days.

(21) Appl. No.: 10/784,337

(22) Filed: Feb. 23, 2004

(65) Prior Publication Data

US 2005/0183259 A1 Aug. 25, 2005

(51) Int. Cl.
*B23P 19/00* (2006.01)

(52) U.S. Cl. .................. 29/283.5; 29/508; 29/515; 29/516; 72/402

(58) Field of Classification Search .............. 29/508, 29/515, 516, 283.5; 72/402; 606/108; 623/1.11
See application file for complete search history.

(56) References Cited

U.S. PATENT DOCUMENTS

| | | | | |
|---|---|---|---|---|
| 3,792,603 A | * | 2/1974 | Orain | 72/402 |
| 4,448,195 A | | 5/1984 | Leveen et al. | 128/344 |
| 4,461,163 A | * | 7/1984 | Kralowetz | 72/402 |
| 4,484,585 A | | 11/1984 | Baier | 128/748 |
| 4,578,982 A | * | 4/1986 | Schrock | 72/402 |
| 4,601,701 A | | 7/1986 | Mueller, Jr. | 604/83 |
| 4,769,005 A | | 9/1988 | Ginsburg et al. | 604/53 |
| 4,776,337 A | | 10/1988 | Palmaz | 128/343 |
| 4,913,141 A | | 4/1990 | Hillstead | 606/108 |
| 4,994,071 A | | 2/1991 | MacGregor | 606/194 |
| 4,998,923 A | | 3/1991 | Samson et al. | 606/194 |
| 5,019,085 A | | 5/1991 | Hillstead | 606/108 |
| 5,092,152 A | * | 3/1992 | Miller et al. | 72/402 |
| 5,122,154 A | | 6/1992 | Rhodes | 606/198 |
| 5,195,984 A | | 3/1993 | Schatz | 606/195 |
| 5,219,355 A | | 6/1993 | Parodi et al. | 606/191 |
| 5,261,263 A | * | 11/1993 | Whitesell | 72/409.19 |
| 5,316,023 A | | 5/1994 | Palmaz et al. | 128/898 |
| 5,397,305 A | | 3/1995 | Kawula et al. | 604/96 |

(Continued)

FOREIGN PATENT DOCUMENTS

DE 297 01 758 5/1997

(Continued)

OTHER PUBLICATIONS

U.S. Appl. 10/657,472, filed Sep. 8, 2003, Eidenschink, et al.

(Continued)

*Primary Examiner*—Jermie E. Cozart
(74) *Attorney, Agent, or Firm*—Merchant & Gould P.C.

(57) ABSTRACT

A stent assembly comprises a rotatable sheath and a stent. The assembly is crimped or reduced in diameter prior to loading onto a catheter by one or more crimping apparatuses. One crimping apparatus comprises a blade having a stepped configuration. A mandrel may be used to support the assembly during crimping. The mandrel may have an expandable region. A protective sheath may be used to protect the stent during crimping and to redirect the crimping forces to desired locations about the assembly.

46 Claims, 18 Drawing Sheets

U.S. PATENT DOCUMENTS

| | | |
|---|---|---|
| 5,449,353 A | 9/1995 | Watanabe et al. |
| 5,477,856 A | 12/1995 | Lundquist |
| 5,571,086 A | 11/1996 | Kaplan et al. ................. 604/96 |
| 5,609,627 A | 3/1997 | Goicoechea et al. ........... 623/1 |
| 5,632,763 A | 5/1997 | Glastra |
| 5,643,278 A | 7/1997 | Wijay |
| 5,644,945 A * | 7/1997 | Baldwin et al. ............... 72/402 |
| 5,672,169 A | 9/1997 | Verbeek ......................... 606/1 |
| 5,681,345 A | 10/1997 | Euteneuer .................. 623/1.11 |
| 5,683,345 A | 11/1997 | Waksman et al. |
| 5,697,971 A | 12/1997 | Fischell et al. |
| 5,725,519 A | 3/1998 | Penner et al. |
| 5,749,825 A | 5/1998 | Fischell et al. |
| 5,755,734 A | 5/1998 | Richter et al. |
| 5,755,735 A | 5/1998 | Richter et al. |
| 5,755,778 A | 5/1998 | Kleshinski |
| 5,772,669 A | 6/1998 | Vrba |
| 5,776,142 A | 7/1998 | Gunderson ................. 623/1.11 |
| 5,788,707 A | 8/1998 | Del Toro et al. .......... 612/1.11 |
| 5,797,952 A | 8/1998 | Klein |
| 5,824,055 A | 10/1998 | Spiridigliozzi et al. ........ 623/1 |
| 5,833,694 A | 11/1998 | Poncet ...................... 623/1.11 |
| 5,873,906 A | 2/1999 | Lau et al. |
| 5,876,374 A | 3/1999 | Alba et al. |
| 5,893,868 A | 4/1999 | Hanson et al. |
| 5,906,640 A | 5/1999 | Penn et al. |
| 5,906,759 A * | 5/1999 | Richter .................. 219/121.63 |
| 5,908,405 A | 6/1999 | Imran et al. |
| 5,921,995 A | 7/1999 | Kleshinski |
| 5,935,161 A | 8/1999 | Robinson et al. |
| 5,941,908 A | 8/1999 | Goldsteen et al. |
| 5,944,727 A | 8/1999 | Ahari et al. ................. 606/108 |
| 5,951,569 A | 9/1999 | Tuckey et al. |
| 5,957,929 A | 9/1999 | Brenneman |
| 5,957,941 A | 9/1999 | Ream ........................ 606/159 |
| 5,961,546 A | 10/1999 | Robinson et al. |
| 5,961,548 A | 10/1999 | Shmulewitz |
| 5,968,052 A | 10/1999 | Sullivan, III et al. ....... 623/1.11 |
| 6,013,092 A | 1/2000 | Dehdashtian et al. |
| 6,017,362 A | 1/2000 | Lau .............................. 623/1 |
| 6,027,460 A | 2/2000 | Shturman .................... 600/585 |
| 6,033,434 A | 3/2000 | Borghi ........................... 623/1 |
| 6,048,361 A | 4/2000 | Von Oepen ..................... 623/1 |
| 6,056,722 A | 5/2000 | Jayaraman .................. 604/102 |
| 6,056,775 A | 5/2000 | Borghi et al. .............. 623/1.16 |
| 6,059,813 A | 5/2000 | Vrba et al. ................... 606/198 |
| 6,066,155 A | 5/2000 | Amann et al. ............... 606/192 |
| 6,071,286 A | 6/2000 | Mawad ....................... 606/108 |
| 6,077,297 A | 6/2000 | Robinson et al. ........... 623/1.11 |
| 6,082,990 A * | 7/2000 | Jackson et al. .............. 425/517 |
| 6,090,127 A | 7/2000 | Globerman ................. 606/194 |
| 6,096,045 A | 8/2000 | Del Toro et al. ........... 606/108 |
| 6,096,073 A | 8/2000 | Webster et al. ............ 623/1.16 |
| 6,099,497 A | 8/2000 | Adams et al. .............. 601/96.01 |
| 6,110,191 A | 8/2000 | Dehdashtian et al. ........ 606/192 |
| 6,117,156 A | 9/2000 | Richter et al. .............. 606/194 |
| 6,120,522 A | 9/2000 | Vrba et al. ................... 606/190 |
| 6,132,450 A | 10/2000 | Hanson et al. .............. 606/198 |
| 6,143,014 A | 11/2000 | Dehdashtian et al. ........ 606/192 |
| 6,146,415 A | 11/2000 | Fitz ............................ 623/1.11 |
| 6,152,944 A | 11/2000 | Holman et al. ............. 623/1.11 |
| 6,165,195 A | 12/2000 | Wilson et al. ............... 606/194 |
| 6,165,210 A | 12/2000 | Lau et al. ................... 623/1.12 |
| 6,176,116 B1 * | 1/2001 | Wilhelm et al. ......... 72/409.12 |
| 6,178,802 B1 * | 1/2001 | Reynolds ..................... 72/402 |
| 6,187,015 B1 | 2/2001 | Brenneman ................. 606/108 |
| 6,190,360 B1 | 2/2001 | Iancea et al. .......... 604/164.09 |
| 6,190,393 B1 | 2/2001 | Bevier et al. ............... 606/108 |
| 6,210,380 B1 | 4/2001 | Mauch ....................... 604/284 |
| 6,210,431 B1 | 4/2001 | Power ........................ 623/1.11 |
| 6,214,036 B1 | 4/2001 | Letendre et al. ........... 623/1.11 |
| 6,221,090 B1 | 4/2001 | Wilson ....................... 606/194 |
| 6,221,097 B1 | 4/2001 | Wang et al. ............... 623/1.11 |
| 6,224,587 B1 | 5/2001 | Gibson ........................ 604/528 |
| 6,238,410 B1 | 5/2001 | Vrba et al. .................. 606/198 |
| 6,246,914 B1 | 6/2001 | De la Rama et al. ....... 607/122 |
| 6,254,593 B1 | 7/2001 | Wilson ...................... 606/1.11 |
| 6,258,052 B1 | 7/2001 | Milo ............................ 604/22 |
| 6,258,073 B1 | 7/2001 | Mauch ........................ 604/284 |
| 6,264,688 B1 | 7/2001 | Herklotz et al. ........... 623/1.16 |
| 6,280,466 B1 | 8/2001 | Kugler et al. .............. 623/1.12 |
| 6,287,277 B1 | 9/2001 | Yan ........................ 604/96.01 |
| 6,287,330 B1 | 9/2001 | Johansson et al. ......... 623/1.13 |
| 6,290,673 B1 | 9/2001 | Shanley ................. 604/102.02 |
| 6,299,636 B1 | 10/2001 | Schmitt et al. .............. 623/1.2 |
| 6,302,906 B1 | 10/2001 | Goicoechea et al. ....... 623/1.11 |
| 6,319,275 B1 | 11/2001 | Lashinski et al. .......... 623/1.11 |
| 6,322,548 B1 | 11/2001 | Payne et al. ................ 604/500 |
| 6,331,186 B1 | 12/2001 | Wang et al. ............... 623/1.11 |
| 6,342,066 B1 | 1/2002 | Toro et al. ................. 623/1.11 |
| 6,350,277 B1 | 2/2002 | Kocur ....................... 623/1.11 |
| 6,360,577 B2 * | 3/2002 | Austin ........................ 72/402 |
| 6,361,544 B1 | 3/2002 | Wilson et al. .............. 606/194 |
| 6,361,555 B1 | 3/2002 | Wilson ....................... 623/1.11 |
| 6,364,893 B1 | 4/2002 | Sahatjian et al. ........... 606/194 |
| 6,371,978 B1 | 4/2002 | Wilson ....................... 623/1.11 |
| 6,375,660 B1 | 4/2002 | Fischell et al. ............. 606/108 |
| 6,379,372 B1 | 4/2002 | Dehdashtian et al. ....... 606/192 |
| 6,387,117 B1 | 5/2002 | Arnold, Jr. et al. .......... 623/1.1 |
| 6,387,120 B2 | 5/2002 | Wilson et al. .............. 623/1.11 |
| 6,391,050 B1 | 5/2002 | Broome ..................... 623/1.11 |
| 6,406,487 B2 | 6/2002 | Brenneman ................ 623/1.11 |
| 6,406,489 B1 | 6/2002 | Richter et al. ............. 623/1.16 |
| 6,416,529 B1 | 7/2002 | Holman et al. ............. 606/194 |
| 6,436,104 B2 | 8/2002 | Hojeibane ................. 606/108 |
| 6,443,880 B2 | 9/2002 | Blais et al. .................. 492/16 |
| 6,443,980 B1 | 9/2002 | Wang et al. ............... 623/1.35 |
| 6,475,166 B1 | 11/2002 | Escano ....................... 600/585 |
| 6,478,814 B2 | 11/2002 | Wang et al. ............... 623/1.12 |
| 6,482,211 B1 | 11/2002 | Choi .......................... 606/108 |
| 6,488,694 B1 | 12/2002 | Lau et al. ................... 606/194 |
| 6,508,835 B1 | 1/2003 | Shaolian et al. ........... 623/1.35 |
| 6,510,722 B1 * | 1/2003 | Ching et al. ................. 72/402 |
| 6,514,261 B1 | 2/2003 | Randall et al. ............. 606/108 |
| 6,514,281 B1 | 2/2003 | Blaeser et al. ............. 623/1.12 |
| 6,517,558 B2 | 2/2003 | Gittings et al. ............. 606/153 |
| 6,520,983 B1 | 2/2003 | Colgan et al. ............. 623/1.11 |
| 6,520,988 B1 | 2/2003 | Colombo et al. .......... 623/1.35 |
| 6,530,947 B1 | 3/2003 | Euteneuer et al. ......... 623/1.11 |
| 6,533,805 B1 | 3/2003 | Jervis ........................ 623/1.11 |
| 6,540,719 B2 | 4/2003 | Bigus et al. ............. 604/96.01 |
| 6,544,278 B1 | 4/2003 | Vrba et al. .................. 606/198 |
| 6,554,841 B1 | 4/2003 | Yang ......................... 606/108 |
| 6,568,235 B1 * | 5/2003 | Kokish ........................ 72/402 |
| 6,582,459 B1 | 6/2003 | Lau et al. ................... 623/1.11 |
| 6,589,262 B1 | 7/2003 | Honebrink et al. ......... 606/191 |
| 6,596,020 B2 | 7/2003 | Vardi et al. ................ 623/1.11 |
| 6,599,315 B2 | 7/2003 | Wilson ....................... 623/1.11 |
| 6,602,226 B1 | 8/2003 | Smith et al. ............ 604/103.05 |
| 6,607,506 B2 | 8/2003 | Kletschka ................ 604/96.01 |
| 6,607,552 B1 | 8/2003 | Hanson ..................... 623/1.11 |
| 6,613,067 B1 | 9/2003 | Johnson ..................... 606/194 |
| 6,623,518 B2 | 9/2003 | Thompson et al. ........ 623/1.11 |
| 6,629,350 B2 * | 10/2003 | Motsenbocker ............ 29/283.5 |
| 6,629,981 B2 | 10/2003 | Bui et al. ................... 606/108 |
| 6,651,478 B1 * | 11/2003 | Kokish ........................ 72/402 |
| 6,660,030 B2 | 12/2003 | Shaolian et al. ........... 623/1.11 |
| 6,669,718 B2 | 12/2003 | Besselink .................. 623/1.11 |
| 6,692,483 B2 | 2/2004 | Vardi et al. ................ 604/529 |
| 6,695,862 B2 | 2/2004 | Cox et al. ................... 606/191 |
| 6,699,275 B1 | 3/2004 | Knudson et al. ........... 623/1.12 |
| 6,739,033 B2 * | 5/2004 | Hijlkema et al. ............ 29/508 |
| 6,925,847 B2 * | 8/2005 | Motsenbocker .............. 72/402 |
| 2001/0001890 A1 | 5/2001 | Austin ........................ 29/282 |

| | | | | | |
|---|---|---|---|---|---|
| 2001/0049548 A1 | 12/2001 | Vardi et al. ............ 623/1.11 | WO | 03/017872 A1 | 3/2003 |
| 2002/0019664 A1 | 2/2002 | Douglas ............... 623/1.35 | WO | 03/055414 | 7/2003 |
| 2002/0019665 A1 | 2/2002 | Dehdashtian et al. ...... 623/1.35 | WO | 03/61529 | 7/2003 |
| 2002/0022874 A1 | 2/2002 | Wilson ............... 623/1.11 | | | |
| 2002/0038140 A1 | 3/2002 | Yang et al. ............ 623/1.12 | | | |
| 2002/0038141 A1 | 3/2002 | Yang et al. ............ 623/1.12 | | | |
| 2002/0072755 A1 | 6/2002 | Bigus et al. ............ 606/108 | | | |
| 2002/0111675 A1 | 8/2002 | Wilson ............... 623/1.35 | | | |
| 2002/0116045 A1 | 8/2002 | Eidenschink ............ 623/1.11 | | | |
| 2002/0120320 A1 | 8/2002 | Wang et al. ............ 623/1.11 | | | |
| 2002/0138966 A1* | 10/2002 | Motsenbocker ............ 29/516 | | | |
| 2003/0023298 A1 | 1/2003 | Jervis ............... 623/1.11 | | | |
| 2003/0055483 A1 | 3/2003 | Gumm ............... 623/1.11 | | | |
| 2003/0055484 A1 | 3/2003 | Lau et al. ............ 623/1.13 | | | |
| 2003/0144671 A1 | 7/2003 | Brooks et al. ............ 606/108 | | | |
| 2003/0181923 A1 | 9/2003 | Vardi ............... 606/108 | | | |
| 2003/0192164 A1* | 10/2003 | Austin ............... 29/505 | | | |
| 2003/0195546 A1 | 10/2003 | Solar et al. ............ 606/192 | | | |
| 2004/0199239 A1* | 10/2004 | Austin et al. ............ 623/1.11 | | | |
| 2004/0260379 A1* | 12/2004 | Jagger et al. ............ 623/1.11 | | | |

FOREIGN PATENT DOCUMENTS

| | | |
|---|---|---|
| FR | 2 678 508 A1 | 1/1993 |
| WO | WO 200211646 A1 * | 2/2002 |

OTHER PUBLICATIONS

U.S. Appl. 10/757,646, filed Jan. 13, 2004, Eidenschink, et al.
U.S. Appl. 10/780,937, filed Feb. 18, 2004, Eidenschink, et al.
U.S. Appl. 10/863,724, filed Jun. 8, 2004, Eidenschink, et al.
Foley et al., "Bifurcation Lesion Stenting", *The Thoraxcentre Journal,* vol. 8, No. 4, (1996).
Schampaert, MD, Erick et al., "The V-Stent: A Novel Technique for Coronary Bifurcation Stenting", *Catheterization and Cardiovascular Diagnosis,* 39:320-363 (1996).
Pomerantz, MD, et al., "Distortion of Palmaz-Schatz Stent Geometry Following Side-Branch Balloon Dilation Through the Stent in a Rabbit Model", *Catheterization and Cardiovascular Diagnosis,* 40:422-426 (1997).
Oda, MD., et al., "Fork Stenting for Bifurcational Lesion", Journal of Interventional Cardiology, vol. 9, No. 6, pp. 445-454 (Dec. 1996).
U.S. Appl. No. 10/375,689, Feb. 27, 2003, Eidenschink.
U.S. Appl. No. 10/747,546, Dec. 29, 2003, Eidenschink et al.

* cited by examiner

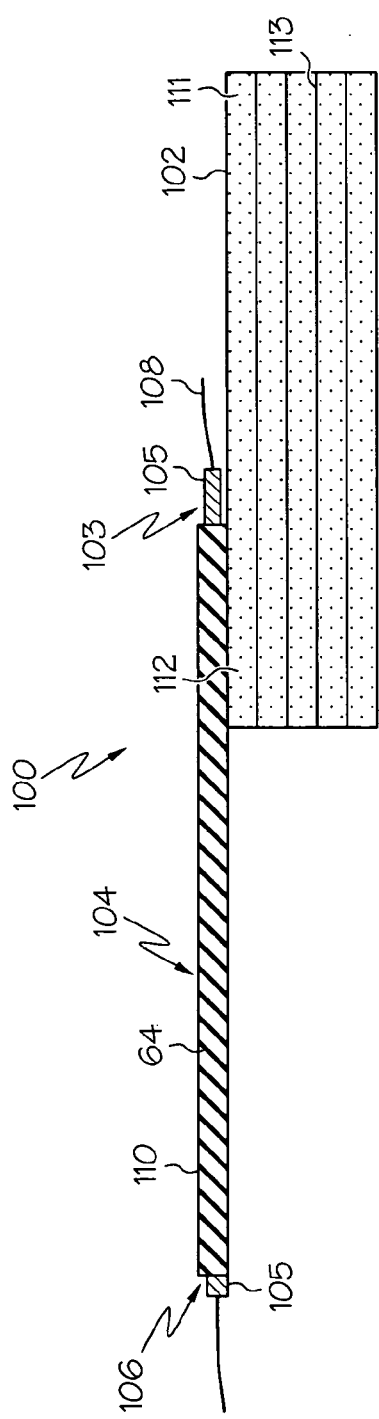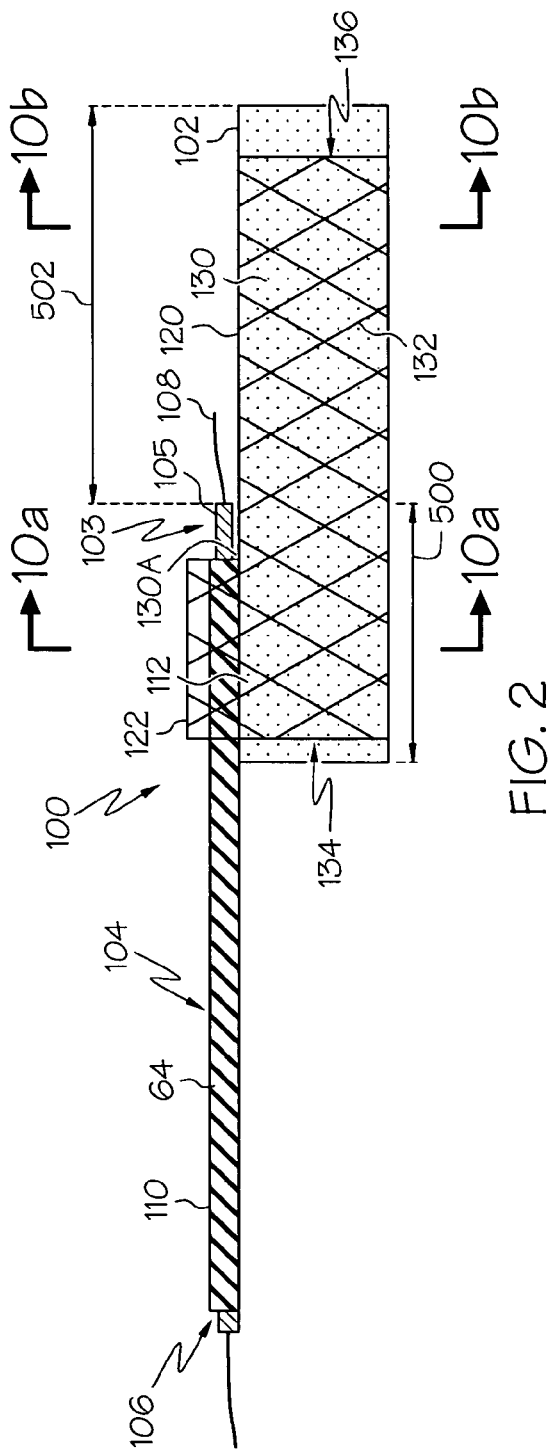

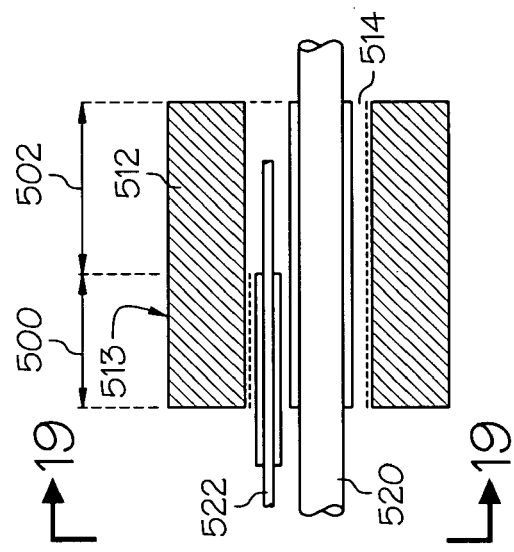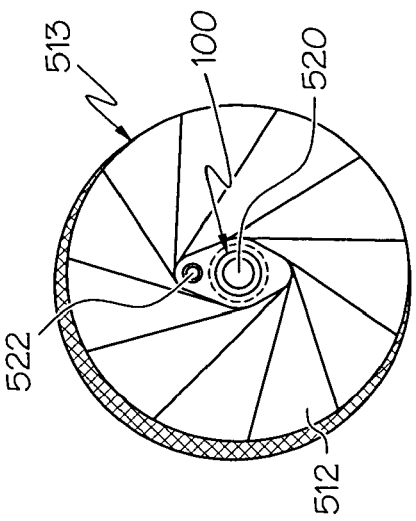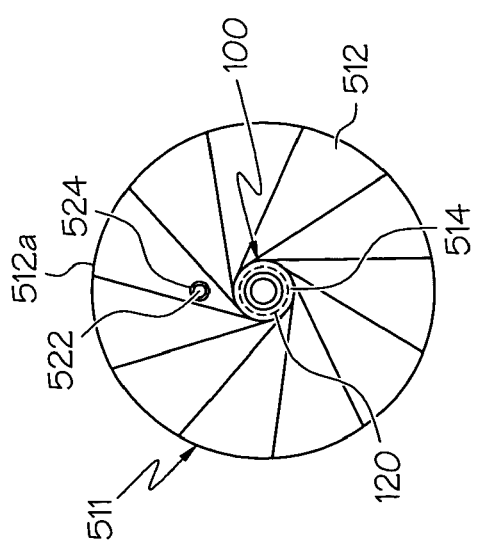

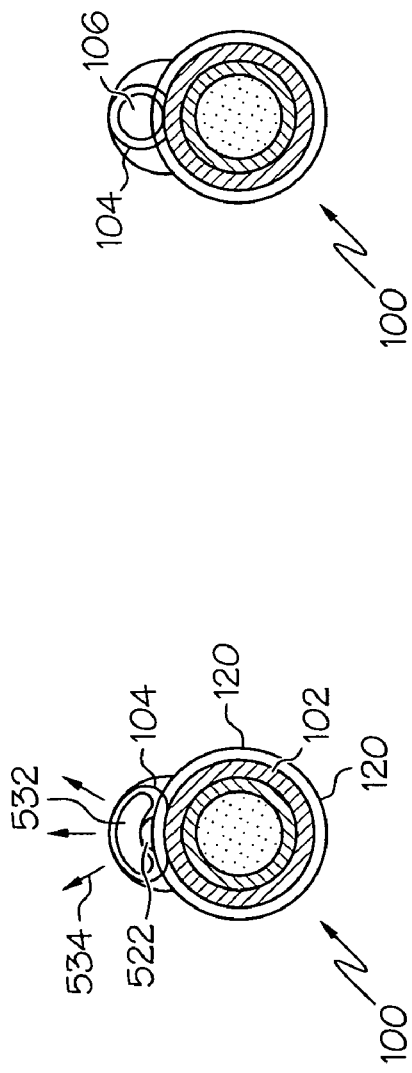
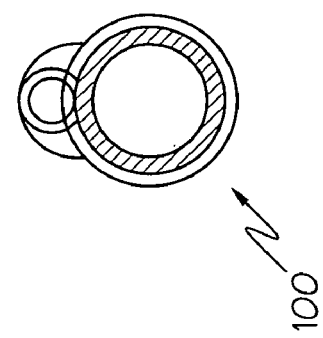
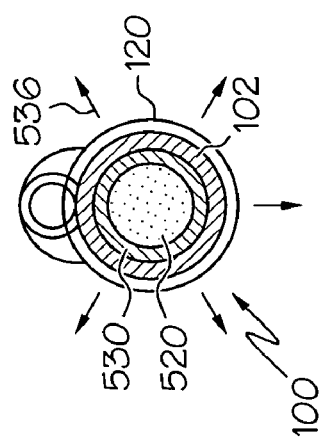

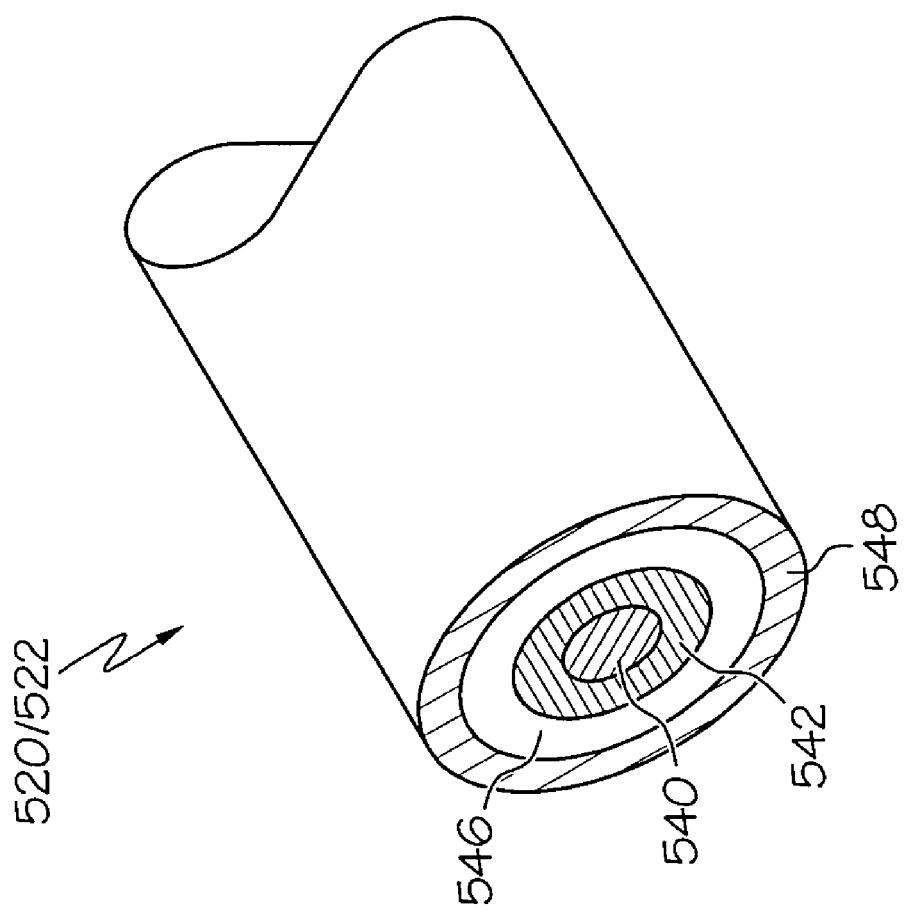

APPARATUS FOR CRIMPING A STENT ASSEMBLY

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Description of the Related Art

A stent delivery system employing a stent assembly with branches intended for deployment in the adjacent branches of a vessel bifurcation has been proposed to allow placement of a portion of the assembly in both a primary passage, such as an artery, and a secondary passage, such as a side branch artery. Additionally, these stents generally have an opening which allows for unimpeded blood flow into the side branch artery. However, problems are still encountered in orienting the stent relative to the side branch at the bifurcation of the primary and secondary passages. Moreover, such bifurcated assemblies are typically specially manufactured at an increased cost over a more standard stent intended for single vessel deployment.

In delivering a stent to a vessel location, many current devices rely on either passive torque (e.g., pushing the stent forward and allowing the stent that is fixed on the guidewire/balloon to passively rotate itself into place) or creating torque from outside of the patient to properly orient the medical device in the passage. These devices and methods of achieving proper angular orientation have not been shown to be effective in properly placing and positioning the stent. In addition, many catheter systems which are currently utilized to deploy a stent or other implantable device into a body lumen do not provide adequate stent edge protection prior to delivery.

Thus, a need exists to provide a catheter which is capable of allowing a medical device such as a stent to be easily maneuvered and aligned at a vessel bifurcation or other location, while also adequately protecting the edges of the stent during advancement of the catheter through the tortuous confines of a body lumen. Various devices and methods described herein address this need by providing a catheter system with a rotatable sheath apparatus which a stent may be mounted on. The rotatable assembly is rotatable about the catheter shaft thereby eliminating the need to apply torque to the catheter shaft to align the stent at a vessel bifurcation.

There is also a need to provide one or more devices and methods for reducing/crimping a stent onto the rotatable sheath without interfering with the performance of the sheath. Existing crimping devices and methods, such as are described in U.S. Pat. No. 6,387,118; U.S. Pat. No. 6,108,886; U.S. Pat. No. 6,092,273; U.S. Pat. No. 6,082,990; U.S. Pat. No. 6,074,381; U.S. Pat. No. 6,063,102; U.S. Pat. No. 5,992,000; etc. are insufficient as the traditional cross-section of the crimping iris or assembly would likely deform and/or damage the unique shape of the rotatable sheath and stent assembly, which is described in greater detail below.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In some embodiments, the present invention is concerned with the crimping and otherwise reducing in size of stents, including drug delivery or coated stents of any configuration or expansion type, including inflation expandable stents, self-expanding stents, hybrid expandable stents, etc. For the purpose of this disclosure, it is understood that the term 'stent' includes stents, stent-grafts, grafts and vena cava filters and other implantable medical devices for luminal support. It is also understood that the term 'crimping' refers to a reduction in size or profile of a stent and/or a device upon or within which it is mounted; and 'crimper' refers to devices for accomplishing such reduction in size or profile of same.

Some embodiments of the invention are especially directed to devices and methods for us in crimping a stent or stent onto rotatable sheath mechanism as described herein as well as in U.S. patent application Ser. No. 10/375,689, filed Feb. 27, 2003 and U.S. patent application Ser. No. 10/657,472, filed Sep. 8, 2003 both of which are entitled Rotating Balloon Expandable Sheath Bifurcation Delivery; U.S. patent application Ser. No. 10/747,546, filed Dec. 29, 2003 and entitled Rotating Balloon Expandable Sheath Bifurcation Delivery System; and U.S. patent application Ser. No. 10/757,646, filed Jan. 13, 2004 and entitled Bifurcated Stent Delivery System, the entire content of each being incorporated herein by reference.

Some embodiments of the present invention are directed to various devices and methods for crimping a stent onto a rotatable sheath in order to provide the resulting rotatable assembly with a reduced profile in order to allow the assembly to be mounted on a catheter shaft and be rotatable thereabout.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

FIG. 1 is a side view of a rotating sheath assembly.

FIG. 2 is a side view of the assembly shown in FIG. 1 shown configured for delivery of a stent.

FIG. 17 is a cross-sectional front view of the embodiment shown in FIGS. 15–16.

FIG. 18 is a cross-sectional side view side view of an embodiment of the invention wherein a different crimping head is utilized to reduce/crimp the proximal portion of the rotatable assembly of FIG. 2.

FIG. 19 is a cross-sectional front view of the embodiment shown in FIG. 18.

FIG. 23 is a cross-sectional view of the embodiment shown in FIG. 20, wherein the secondary mandrel is expanded following reduction/crimping of the rotatable assembly.

FIG. 24 is a cross-sectional view of the embodiment shown in FIG. 23 shown with the secondary mandrel removed and secondary guidewire housing in place.

FIG. 25 is a cross-sectional view of the embodiment shown in FIG. 24 wherein the primary mandrel is optionally expanded to assist in removal of the rotatable assembly from the primary mandrel following reduction/crimping.

FIG. 26 is a cross-sectional view of the embodiment shown in FIG. 24 wherein the rotatable assembly is shown removed from the mandrel(s) following reduction/crimping.

FIG. 27 is a perspective cross-section of an embodiment of the invention comprising a configuration of one or both mandrels shown in FIGS. 20–26.

DETAILED DESCRIPTION OF THE INVENTION

Figure 3:
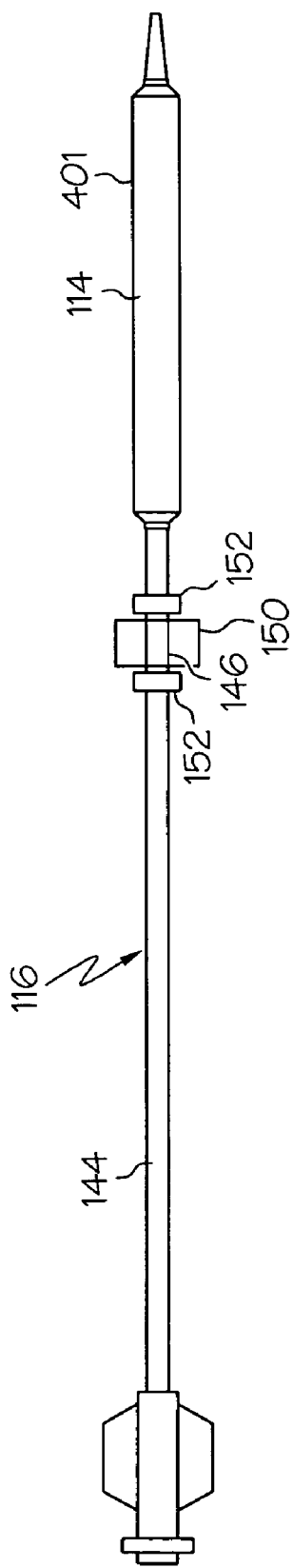
FIG. 3 is a side view of a catheter assembly. The catheter assembly is provided with a rotating collar.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 4:
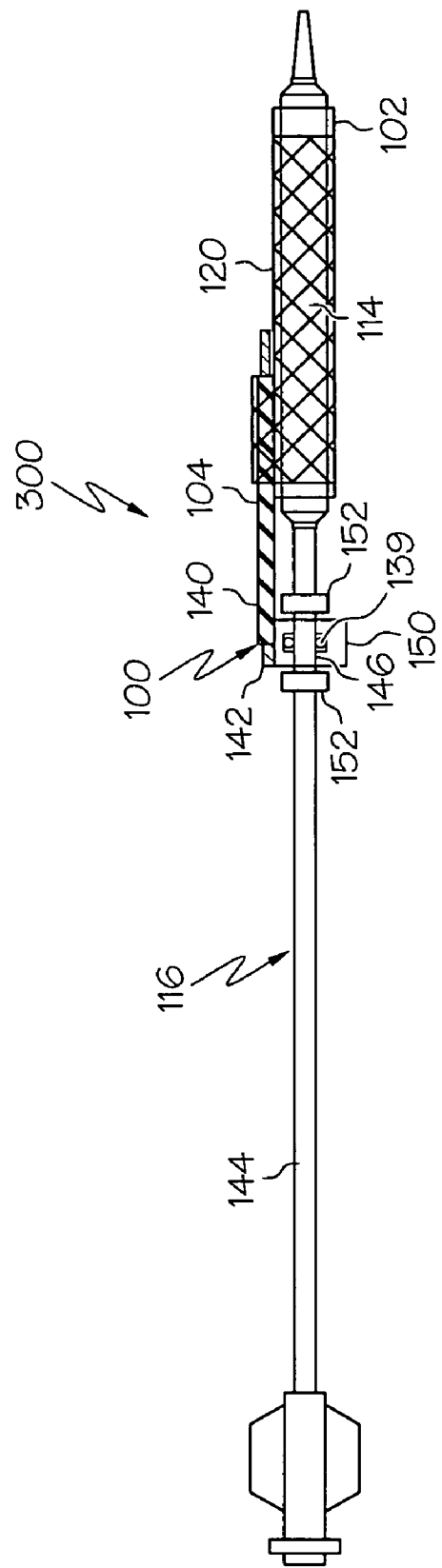
FIG. 4 is a side view of the catheter assembly of FIG. 3 with the rotating sheath assembly and stent of FIG. 2 mounted thereon.
Figure 5:
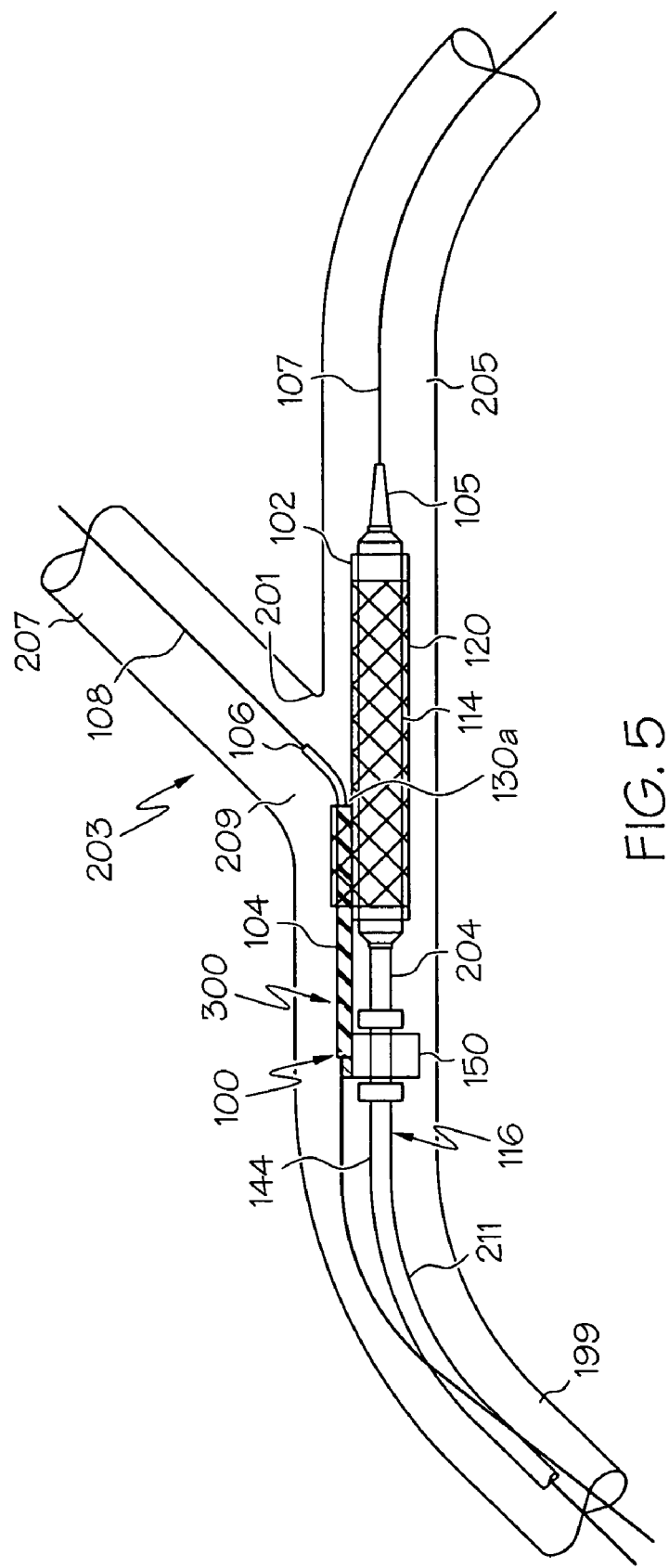
FIG. 5 is a side view of the catheter assembly of FIG. 4 shown being advanced along a guidewire to a vessel bifurcation prior to delivery of the stent.

Referring now to the drawings which are for the purposes of illustrating embodiments of the invention only and not for purposes of limiting same, FIGS. 1–2 illustrate a an assembly 100 for use in a stent delivery system 300 which is mounted on a catheter body 116, such as is depicted in FIGS. 3–5, to provide the system with a rotating region that allows a stent, such as is shown in FIGS. 6–9, to be properly aligned in a vessel bifurcation. Some additional examples of such assemblies are shown and described in U.S. patent application Ser. No. 10/375,689, filed Feb. 27, 2003 and U.S. patent application Ser. No. 10/657,472, filed Sep. 8, 2003 both of which are entitled Rotating Balloon Expandable Sheath Bifurcation Delivery; U.S. patent application Ser. No. 10/747,546, filed Dec. 29, 2003 and entitled Rotating Balloon Expandable Sheath Bifurcation Delivery System; and U.S. patent application Ser. No. 10/757,646, filed Jan. 13, 2004 and entitled Bifurcated Stent Delivery System.

The rotating sheath assembly 100 depicted in FIGS. 1–2 comprises a tubular sleeve or sheath 102 and a positioning or secondary guidewire housing 104. The housing 104 defines a secondary guidewire lumen 106 through which a secondary guidewire 108 may be passed.

Though the housing 104 may be constructed of a wide variety of materials including one or more metals, plastics, etc., in some instances the housing 104 may be and/or include an external reinforcing member or hypotube 64.

The hypotube 64 may comprise stainless steel, one or more polymer materials or other material. To improve flexibility, in some cases the housing 104 is provided with one or more openings 110 along its length. For example, the housing 104 may be spiral cut to provide at least a continuous opening 110 which acts to provide improve the flexibility of the housing 104. In some embodiments the housing may by provided with a plurality alternating 'C' cuts or otherwise cut to provide improved flexibility.

The assembly 100 may include a secondary guidewire housing 104 which further comprises an inner shaft 103, about which the hypotube 64 is disposed. The inner shaft 103 may be a flexible hollow tubular member which extends distally beyond the distal end of the hypotube 64. This distal and/or proximal tips 105 of the inner shaft 103 provides the housing with a flexible protective sheath about the guidewire 108 as it passes out of the secondary guidewire lumen 106. Such a protective covering prevents the guidewire 108 from excessively rubbing against the wall 201 of the vessel 199, such as in the manner depicted in FIG. 5; even where the secondary guidewire 108 exits the secondary lumen 106 at a significant angle. The inner shaft 103 may be constructed of any of a variety of flexible materials such as: HDPE, PEBAX, nylon, urethane, and/or other materials in a single layer, multi-layer and/or braided configuration.

In many catheters, the shaft 144 of the catheter 116 defines a primary guidewire housing 211 through which a primary guidewire 107 may be advanced. In use, guidewires 107 and 108 are passed through a lumen or other body vessel 209 to a bifurcation 203. Primary guidewire 107 is then advanced into a primary branch of passage 205 of the bifurcation 203 while the secondary guidewire 108 is advanced into the adjacent or secondary branch 207 of the bifurcation 203. As the system is advanced along both guidewires 107 and 108, as a result of the divergent paths defined by the guidewires 107 and 108, the rotatable sleeve 104 will rotate the stent 120 into a desired position so that the secondary opening 130a of the stent is aligned with the secondary passage 207. Where the catheter 116 is a fixed wire system, the use of the primary guidewire is unnecessary.

Examples of the rotating assembly 100 include a distal portion of the housing 104 being engaged to at least a proximal portion of the sheath 102 at an engagement site 112. The manner or mechanism of engagement between the sheath and housing 104 may be by bonding, welding, adhering adhesively engaging, mechanically engaging or otherwise connecting the surfaces of the respective sheath 102 and housing 104.

The sheath 102 is a hollow tube of sheath material that is configured to be placed over the balloon 114 or other region of a catheter 116, such as in the manner illustrated in FIGS. 3 and 4. The sheath 102 is further configured to be rotatable about the catheter shaft and/or balloon 114, even when a stent 120 has been positioned about and/or affixed to the sheath 102.

In order to ensure that the sheath 102 is rotatable about a balloon 114 and/or other region of a catheter, even with a stent 120 crimped on to the sheath 102 and the catheter is being advanced through the a body, the sheath 102 may be constructed of a variety of low friction materials such as PTFE, HDPE, etc. In at least one embodiment the sheath 102 is at least partially constructed of a hydrophilic material, such as hydrophilic polymers such as; TECOPHILIC® material available from Thermedics Polymer Products, a division of VIASYS Healthcare of Wilmington, Mass.; TECOTHANE®, also available from Thermedics Polymer Products; hydrophilic polyurethanes, and/or aliphatic, polyether-based thermoplastic hydrophilic polyurethane; and any other material that provides the sheath 102 with the ability to rotate freely about the balloon 114 when in the "wet" state, such as when the catheter is exposed to body fluids during advancement through a vessel. Suitable sheath materials may also provide the sheath with rotatability in the "dry", or pre-insertion, state, but with the application of a greater amount of force than when in the wet state, such materials are referred to herein as being tecophilic.

A sheath 102 at least partially constructed from tecophilic material provides the sheath 102 with the ability to rotate freely about the balloon 114 when in the "wet" state, such as when the catheter is exposed to body fluids during advancement through a vessel. The tecophilic sheath 102 is also capable of rotation in the "dry", or pre-insertion, state, but with the application of a greater amount of force than when in the wet state.

In some cases the sheath 102 may be constructed of one or multiple materials, in one or more layers. For example, the sheath 102 may comprise an outer layer of a softer material than that of the material used in constructing an inner layer, such as has been previously described. In some embodiments, an example of which is shown in FIG. 1, the sheath 102 may be comprised of a matrix of a first material 111 and have one or more supportive stripes, strands, members or areas of a second supportive material 113 within, external to or internal to such a matrix.

The composition of the sheath 102 material, whether a single, multiple layer or stripe reinforced extrusion may include essentially any appropriate polymer or other suitable materials. Some example of suitable polymers include Hydrophilic Polyurethanes, Aromatic Polyurethanes, Polycarbonate base Aliphatic Polyurethanes, Engineering polyurethane, Elastomeric polyamides, block polyamide/ethers, polyether block amide (PEBA, for example available under the trade name PEBAX), and Silicones, Polyether-ester (for example a polyether-ester elastomer such as Arnitel available from DSM Engineering Plastics), Polyester (for example a polyester elastomer such as Hytrel available from Du Pont), or linear low density polyethylene (for example Rexell).

Example of suitable re-enforcing materials whether alone or blended with other materials, mixtures or combination or copolymers include all Polyamides (for example, Durethan available from Bayer or Cristamid available from ELF Atochem), polyethylene (PE). Marlex high-density polyethylene, polyetheretherketone (PEEK), polyimide (PI), and polyetherimide (PEI), liquid crystal polymers (LCP), and Acetal (Delrin or Celcon).

Often the inner surface of the sheath 102 or the outer surface of the balloon 114 may include a coating of one or more low friction materials or include one or more low friction materials in its construction. Such a coating 401 is shown in FIG. 3, as being depicted on the surface of the balloon 114 before assembly 100 has been placed thereabout, such as is depicted in FIG. 4. Coating 401 may however by placed between the balloon 114 and sheath 102 at any time. Some examples of a suitable coating material include but are not limited to: hydrogel, silicon, and/or BIOSLIDE® available from SciMed Life Systems, Inc. of Maple Grove Minn.

As mentioned above, the sheath 102 is configured to be freely rotatable about a balloon of a catheter even when a stent 120, such as is shown in FIGS. 2 and 4 is crimped onto the sheath 102. When properly positioned on the sheath 102, a proximal portion 122 of the stent 120 is also disposed about at least a portion of the secondary guidewire housing 104. When properly positioned about the sheath 102 and the housing 104, at least a portion of the housing 104 and/or the secondary guidewire 108 extends distally through a cell opening 130 of the stent 120.

Figure 6:
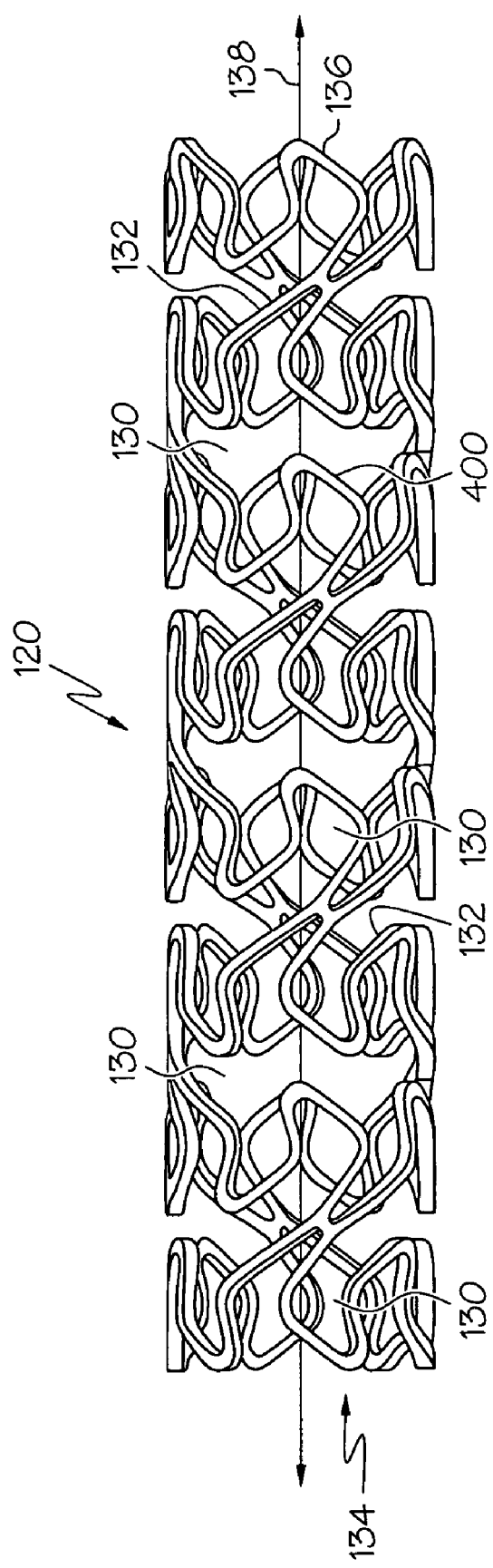
FIG. 6 is a side view of a stent, such as that shown in FIG. 2.

Stent 120 may be a stent, such as is shown in FIG. 6, which is at least partially constructed of a plurality of interconnected struts, connectors or members 132. The stent 132 defines a proximal opening 134, a distal opening 136 and a flow path 138 therebetween. The cell openings 130 are in fluid communication with the flow path 138.

When the secondary guidewire 108 and/or the secondary guidewire housing 104 is threaded through one of the cell openings 130 when the stent is positioned onto the assembly 100, such as is shown in FIGS. 2 and 4, the members 132 that define the selected cell opening 130a, as well as the shape of the opening 130a through which the secondary guidewire 108 exits the stent, may be distorted or modified in order to accommodate the passage of secondary guidewire 108 and/or the secondary guidewire housing 104 therethrough.

Figure 7:
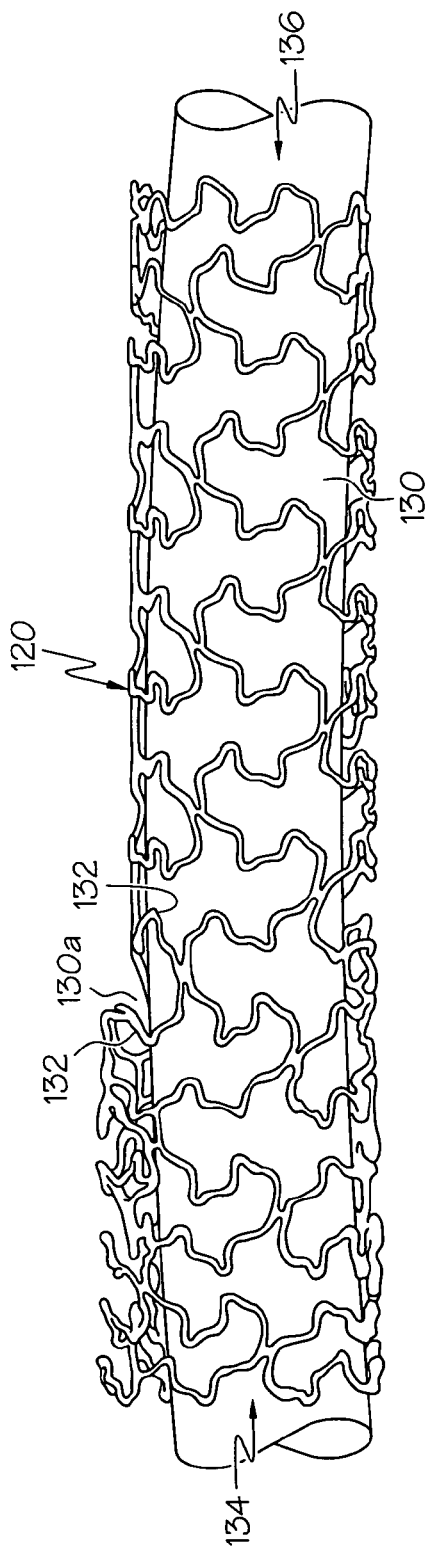
FIG. 7 is a side perspective view of the stent shown in FIG. 6 wherein a side branch opening is shown formed from the enlargement of a cell opening in the stent wall.
Figure 8:
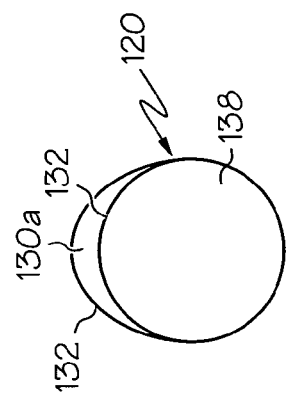
FIG. 8 is a cross-sectional view of the stent of FIG. 7.

The modified cell opening 130a, hereinafter referred to as secondary opening 130a, is positioned on the stent 120 between the proximal opening 134 and the distal opening 136. The manner in which the secondary opening 130a, the members 132 adjacent thereto, and to an extent the stent 120 itself, are modified or distorted by the position of the secondary guidewire and/or secondary guidewire housing is depicted in FIGS. 7 and 8.

It should be noted that when the stent 120 is placed on the assembly in the manner described above, the distortion of the secondary opening 130a and the adjacent members 132 is of a minimal extent, and is provide only to allow sliding passage of the secondary guidewire 108, and if desired a distal portion of the secondary guidewire housing 104, through the secondary opening 130a. As such, the actual size of the secondary opening 130a may be substantially similar, or only marginally different than that of the surrounding cell openings 130.

It should also be further noted that while stent 120 may be a standard "single vessel" stent that is provided with a secondary opening 130a in the manner described above, the stent 120 may also be a bifurcated stent having a trunk or stem portion, with one or more leg portions and/or branch openings adjacent thereto, through one of which the secondary guidewire may be passed. Such bifurcated stents and stent assemblies are well known in the art.

Figure 9:
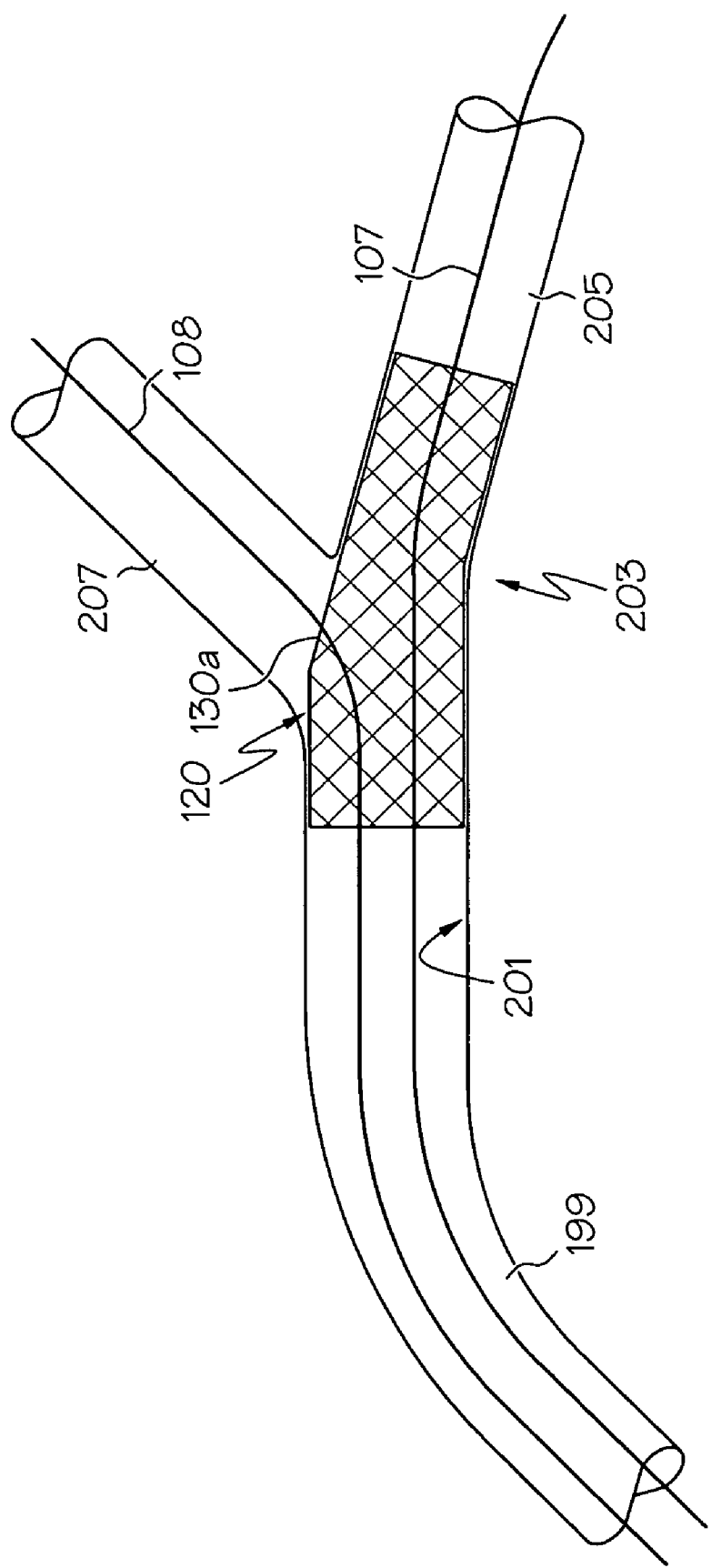
FIG. 9 is a side view of the stent depicted in FIG. 5, wherein the stent has been delivered from the catheter assembly, by balloon expansion and the assembly subsequently withdrawn from the vessel(s).

In some cases, the stent 120, or one or more portions thereof, may be configured to deliver one or more therapeutic agents to a delivery site such as within the vessel 199 or one or more areas adjacent thereto, such as shown in FIGS. 5 and 9. To better accommodate placement of a therapeutic agent on the stent 120, in some instances one or stent members 132, such as is shown in FIG. 6, maybe configured to include one or more holes, notches, or other surface features to which one or more therapeutic agents 400 may be placed for delivery to the aneurysm site. A therapeutic agent may be placed on the stent in the form of a coating. Often the coating includes at least one therapeutic agent and at least one polymer.

A therapeutic agent may be a drug, a non-genetic agent, a genetic agent, etc. Some examples of suitable non-genetic therapeutic agents include but a re not limited to: anti-thrombogenic agents such as heparin, heparin derivatives, urokinase, and PPack (dextrophenylalanine proline arginine chloromethylketone); anti-proliferative agents such as enoxaprin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine and ropivacaine; anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters, vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin; bifunctional molecules consisting of an antibody and a cytotoxin; cholesterol-lowering agents; vasodilating agents; and agents which interfere with endogenous vasoactive mechanisms, and any combinations thereof.

Where an agent includes a genetic therapeutic agent, such a genetic agent may include but is not limited to: anti-sense DNA and RNA; DNA coding for anti-sense RNA, tRNA or rRNA to replace defective or deficient endogenous molecules; angiogenic factors including growth factors such as acidic and basic fibroblast growth factors, vascular endothelial growth factor, epidermal growth factor, transforming growth factor $\alpha$ and $\beta$, platelet-derived endothelial growth factor, platelet-derived growth factor, tumor necrosis factor $\alpha 1$, hepatocyte growth factor and insulin like growth factor; cell cycle inhibitors including CD inhibitors, thymidine kinase ("TK") and other agents useful for interfering with cell proliferation; at least one of the family of bone morphogenic proteins ("BMP's") such as BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Any of BMP-2, BMP-3, BMP-4, BMP-5, BMP-6 and BMP-7; dimeric proteins such as homodimers, heterodimers, or combinations thereof, alone or together with other molecules; molecules capable of inducing an upstream or downstream effect of a BMP such as "hedgehog" proteins, or the DNA's encoding them and any combinations thereof.

Where a therapeutic includes cellular material, the cellular material may include but is not limited to: cells of human origin (autologous or allogeneic); cells of non-human origin (xenogeneic) and any combination thereof. Some examples of cellular material include but are not limited to the following:

SP—(side population cells) These cells are thought to be some of the most primitive adult stem cells. They are isolated by a specific FACS technique utilizing the ability of SP cells to exclude Hoechst dye from the nucleus. In addition to bone marrow, SP cells have been isolated from most tissues, including: cardiac and skeletal muscle. By the more common surface protein identification these cells are $Lin^-$, $Sca-1^+$, $c-Kit^+$, $CD43^+$, $CD45^+$, $CD34^-$ $Lin^-$—(lineage negative cells) This group of cells is isolated from the bone marrow and all cells which have differentiated to a specific lineage (e.g. red blood cells) have been removed. Therefore leaving all of the stem and progenitor cells. This is beneficial because all primitive cells remain, but may reduce efficiency by including irrelevant, primitive cell types.

$Lin^-CD34^-$—Although $CD34^+$ cells have received much attention, many articles have been published lately which suggest the most primitive bone marrow derived stem cells are $CD34^-$ $Lin^-CD34^+$—Presence of the cell surface protein CD34 has been used to identify hematopoietic stem cells. However, the marker is also present on progenitor cells and white blood cells of various levels of maturity.

Lin⁻cKit⁺—cKit is the cell surface receptor for stem cell factor, and therefore a logical choice for stem cell selection. Most widely studied from bone marrow sources, but have also been isolated from the heart.

MSC—(mesenchymal stem cells) Named so because ordinarily these cells differentiate into cells of mesenchymal tissues (e.g. bone, cartilage, fat), but may also differentiate into cardiomyocytes under certain conditions. Easily isolated from bone marrow and, unlike hematopoietic stem cells, proliferate in vitro. A subpopulation of MSCs has been shown to self-renew faster and have a greater potential for multipotential differentiation than the general MSC population. D. Prockop from Tulane U. is publishing in this area.

Cord Blood Cells—Derived from the blood remaining in the umbilical vein following child birth. This blood has been shown to contain a higher percentage of immature stem cells or progenitor cells. Typically, a matched donor must be found for patients, but a lower incidence of graft versus host disease compared to stem cell isolation from adult blood has been reported. Disadvantages include: insufficient cell number in small blood volumes, unforeseen congenital defects, and contamination by mother's blood which is likely not HLA matched.

Cardiac or other tissue derived stem cells—Most work to date has focused on isolating stem cells from bone marrow. This is due to extensive work in improving bone marrow transplants for chemotherapy and leukemia treatments. However, there is evidence that similar stem cells which can be identified by similar means (e.g. SP, cKit) can be isolated from other tissues (e.g. fat, cardiac muscle).

Whole bone marrow—An "it's in there" approach where whole bone marrow (filtered for bone particles) is transplanted. Benefits include: little processing, all stem and progenitor cells are present, and matrix proteins and growth factors may also be present. Downside—if one or two stem cell types are responsible for cardiac improvement they will only be present in very low numbers.

BM-MNCs—(bone marrow mononuclear cells) Separated from whole bone marrow by a density gradient centrifugation procedure, this population contains non-granular white blood cells, progenitor cells, and stem cells.

EPCs—(endothelial progenitor cells) Isolated from bone marrow based on cell surface markers, these cells will become endothelial cells. In theory, these cells will form new blood vessels when delivered to ischemic tissue.

Skeletal myoblasts—(or satellite cells) These cells are responsible for the regeneration of skeletal muscle following injury. They have the ability to fuse with other myoblasts or damaged muscle fibers. Cardiac muscle therapies assume these cells can integrate into the host tissue and improve tissue properties or functionally participate in contraction.

MDCs—(muscle derived cells) A population of cells isolated from adult skeletal muscle which are similar to myoblasts. The isolation technique preplating entails collecting cells which attach to culture dishes at different times after biopsy. Cells with the best potential plate in the $6^{th}$ group and takes several days to obtain. Investigators working with these cells claim they are a refined population of myoblasts and should result in higher engraftment efficiencies and efficacious procedures.

Go cells—Recently isolated from adult skeletal muscle, these non-satellite cells express GATA-4 and, under certain in vitro growth conditions, progress to spontaneously beating cardiomyocyte-like cells.

Endothelial cells—Transplantation of autologous endothelial cells along with a fibrin matrix induced angiogenesis and improved cardiac function in an ischemic sheep model.

Adult Cardiomyocytes

Fibroblasts—Easily obtained from adult tissues, fibroblasts may provide growth factors or participate in the would healing response. Fibroblast play a critical role in wound healing; the synthesis and deposition of extra cellular matrix. Fibroblasts commonly become contractile in wound healing environments.

Smooth muscle cells—Isolated from arteries, these cells may participate or encourage angiogenesis and/or beneficial cardiac remodeling following MI.

MSCs +5-aza—Culture of mesenchymal stem cells with 5-aza forces differentiation into cardiomyocytes. These cells beat spontaneously after treatment.

Adult cardiac fibroblasts +5-aza—In theory, in vitro treatment of cardiac fibroblasts with 5-aza will result in differentiation into myogenic cells.

Genetically modified cells—Isolation of cells from the patient and genetically modifying them in vitro to encourage production of proteins or differentiation into a cell type which will be beneficial for treating heart failure.

Tissue engineered grafts—Isolation of cells from the patient which are then seeded onto and cultured within resorbable scaffolds (e.g. collagen, PLGA). These cell seeded constructs are then implanted into the patient.

MyoD scar fibroblasts—MyoD family of transcription factors prompt skeletal muscle cell differentiation in fibroblasts. Procedure involves isolation of cardiac scar fibroblasts, genetic transfection with MyoD in vitro and delivery of the cells to the heart to encourage myogenesis.

Pacing cells—Genetically modified fibroblasts which become electrically conducting and signal generators.

Embryonic stem cell clones—Use of cloning technology to produce cardiomyocytes, progenitors, or stem cells which are genetically identical to the patient.

Embryonic stem cells—These cells are the most primitive of cells and will differentiate into functional cardiomyocytes under certain conditions. Both political and technological hurdles must be overcome before commercialization of this technology.

Fetal or neonatal cells—Isolated from the heart of donors, these cells may incorporate into host tissue without immune rejection. Some cardiomyocyte progenitor cells must be present due to the continued growth of the heart in fetal and neonatal humans.

Immunologically masked cells—Allogeneic cell sources (e.g. donor cardiomyocytes) are currently unfeasible due to immune rejection. However, masking technologies have been developed which could make this technology feasible.

Tissue engineered grafts—Isolation of cells from a donor which are then seeded onto and cultured within resorbable scaffolds (e.g. collagen, PLGA). These cell seeded constructs are then implanted into the host or recipient.

Genetically modified cells—Isolation of cells from a donor and genetically modifying them in vitro to encourage production of proteins or differentiation into a cell type which will be beneficial for treating heart failure. The modified cells will then be transplanted into the host or patient.

Teratoma derived cells—A teratocarcinoma is a form of cancer in which the tumor is composed of a heterogeneous mixture of tissues. Through isolation of cells from this tumor and in vitro manipulation and culture a neuronal cell line has been developed. Layton Biosciences has successfully used these cells to form new brain tissue in stroke patients. Similar techniques may be used to produce a myogenic cell line.

Where a therapeutic agent comprises at least one polymer agent or coating, the at least one coating may include but is not limited to: polycarboxylic acids; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers such as EVA; polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; proteins; polypeptides; silicones; siloxane polymers; polylactic acid; polyglycolic acid; polycaprolactone; polyhydroxybutyrate valerate and blends and copolymers thereof; coatings from polymer dispersions such as polyurethane dispersions (BAYHDROL®, etc.), fibrin, collagen and derivatives thereof; polysaccharides such as celluloses, starches, dextrans, alginates and derivatives; hyaluronic acid; squalene emulsions; polyacrylic acid, a copolymer of polylactic acid and polycaprolactone; medical-grade biodegradable materials such as PGA-TMC, Tyrosine-Derived Polycarbonates and arylates; polycaprolactone co butyl acrylate and other co polymers; Poly-L-lactic acid blends with DL-Lactic Acid; Poly(lactic acid-co-glycolic acid); polycaprolactone co PLA; polycaprolactone co butyl acrylate and other copolymers; Tyrosine-Derived Polycarbonates and arylate; poly amino acid; polyphosphazenes; polyiminocarbonates; polydimethyltrimethylcarbonates; biodegradable CA/PO$_4$'s; cyanoacrylate; 50/50 DLPLG; polydioxanone; polypropylene fumarate; polydepsipeptides; macromolecules such as chitosan and Hydroxylpropylmethylcellulose; surface erodible material; maleic anhydride copolymers; zinc-calcium phosphate; amorphous polyanhydrides; sugar; carbohydrate; gelatin; biodegradable polymers; and polymers dissolvable in bodily fluids; and any combinations thereof.

In some instances a suitable polymer agent or coating comprises block copolymers comprising at least one A block and at least one B block. The A blocks are preferably soft elastomeric blocks, which are based upon one or more polyolefins, or other polymer with a glass transition temperature at or below room temperature. For example, the A blocks can be polyolefinic blocks having alternating quaternary and secondary carbons of the general formulation: —(CRR'—CH$_2$)$_n$—, where R and R' are, independently, linear or branched aliphatic groups such as methyl, ethyl, propyl, isopropyl, butyl, isobutyl and so forth, or represent cyclic aliphatic groups such as cyclohexane, cyclopentane, and the like, either with or without pendant groups. Preferred polyolefinic blocks include polymeric blocks of isobutylene,

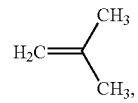

(i.e., polymers where R and R' are methyl groups). Other examples of A blocks include silicone rubber blocks and acrylate rubber blocks.

The B blocks are preferably hard thermoplastic blocks with glass transition temperatures significantly higher than the elastomeric A blocks which, when combined with the soft A blocks, are capable of, inter alia, altering or adjusting the hardness of the resulting copolymer to achieve a desired combination of qualities. Examples of B blocks include polymers of methacrylates or polymers of vinyl aromatics. More specific examples of B blocks include blocks that are (a) formed from monomers of styrene

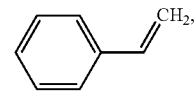

styrene derivatives (e.g., α-methylstyrene, ring-alkylated styrenes or ring-halogenated styrenes or other substituted styrenes where one or more substituents are present on the aromatic ring) or mixtures of the same, collectively referred to herein as "styrenic blocks" or "polystyrenic blocks" or are (b) formed from monomers of methylmethacrylate, ethylmethacrylate, hydroxyethyl methacrylate or mixtures of the same.

The block copolymers are provided in a variety of architectures, including cyclic, linear, and branched architectures. Branched architectures include star-shaped architectures (e.g., architectures in which three or more chains emanate from a single region), comb architectures (e.g., copolymers having a main chain and a plurality of side chains), and dendritic architectures (including arborescent or hyperbranched copolymers).

Some specific examples of such block copolymers include the following:
  (a) BA (linear diblock), (b) BAB or ABA (linear triblock), (c) B(AB)$_n$ or A(BA)$_n$ (linear alternating block), or (d) X-(AB)$_n$ or X-(BA)$_n$ (includes diblock, triblock and other radial block copolymers), where n is a positive whole number and X is a starting seed, or initiator, molecule. One specific group of polymers have X-(AB)$_n$ structures, which are frequently referred to as diblock copolymers and triblock copolymers where n=1 and n=2, respectively (this terminology disregards the presence of the starting seed molecule, for example, treating A-X-A as a single A block, with the triblock therefore denoted as BAB). A particularly beneficial polymer from this group is polystyrene-polyisobutylene-polystyrene triblock copolymer (SIBS). Where n=3 or more, these structures are commonly referred to as star-shaped block copolymers. Other examples of block polymers include branched block copolymers such as dendritic block copolymers, wherein at least one of the A and B blocks is branched, for instance, where the A blocks are branched and are capped by the B blocks.

Once the stent 120 is positioned on the assembly 100, such as in the manner shown in FIG. 2, the assembly 100 may be slid onto a catheter 116, such as is shown in FIGS. 3–4 so that the sheath 102 is rotatingly disposed about the balloon 114 and a proximal portion 140 of the secondary guidewire housing 104 is engaged to a rotating collar 150.

The collar 150 is engaged to the proximal portion 140 of the secondary guidewire housing 104 by any engagement mechanism desired, such as welding, bonding, mechanical engagement, adhesive engagement, etc. As shown in FIG. 4 for example, the proximal portion 140 of the secondary guidewire housing 104 and the collar 150 are engaged externally at engagement site 142. Alternatively, the secondary guidewire housing 104 may be passed at least partially through the collar 150, and/or the collar 150 may define a lumen through which the secondary guidewire 108 may be passed before entering into the secondary guidewire housing 104.

Collar 150 may be a substantially cylindrical member that is disposed about the shaft 144 of the catheter 116 at a position proximal of the balloon 114. The collar 150 may be characterized as defining a catheter shaft lumen 146 through which the catheter shaft 144 is passed. In order to provide the collar 150 with the ability to freely rotate about the catheter shaft 144, the collar 150 defines a catheter shaft lumen 146 which has a diameter greater than the outer diameter of the shaft 144. In some embodiments one or more lubricious substances may be placed between the collar 150 and the shaft 144 to further encourage free rotation therebetween.

While the rotating collar 150 is free to rotate about the shaft 144, in some embodiments it will also be capable of being longitudinally displaced along the shaft 144 as well. As such, in some embodiments one or more locks or hubs 152 may be affixed about the shaft 144 on one or both sides of the collar 150 to prevent or limit the potential longitudinal displacement of the collar 150 relative to the shaft 144.

As is shown in FIG. 5, when the assembly 100, including the stent 120 is placed on the catheter 116, the combined system 300 is ready for use in a stent delivery procedure. However, in some cases it may be necessary to provide the system 300 with one or more stent retaining elements to retain or aid in retaining the stent in place about the sheath 102. In light of the above, however, such elements must be configured so as to not unduly interfere with the rotatability of the assembly 100 about the catheter 116.

Figure 10B:
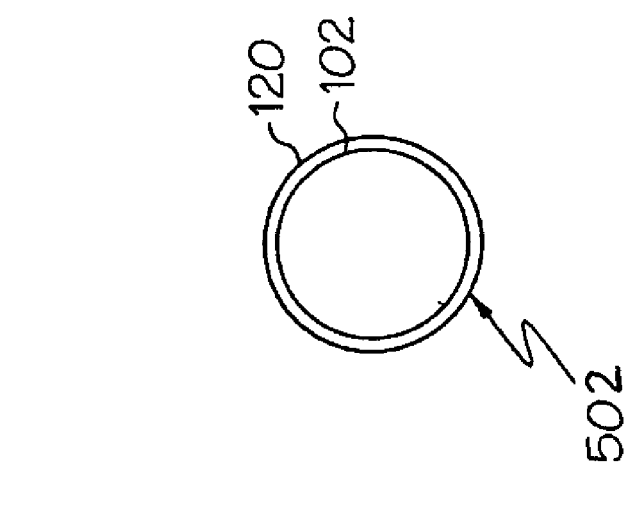
FIG. 10b is a cross-sectional front view of a second region of the rotatable assembly shown in FIG. 2 corresponding to section line 'B'.
Figure 10A:
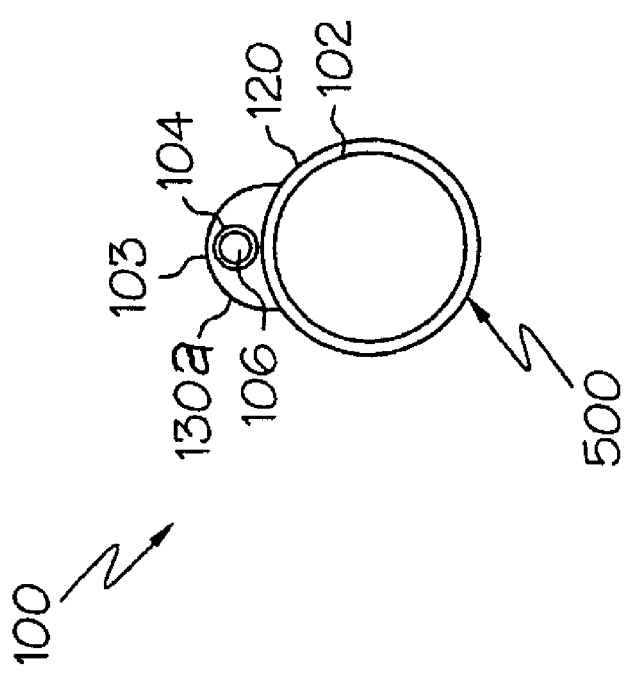
FIG. 10a is a cross-sectional front view of a first region of the rotatable assembly shown in FIG. 2 corresponding to section line 'A'.
Figure 11B:
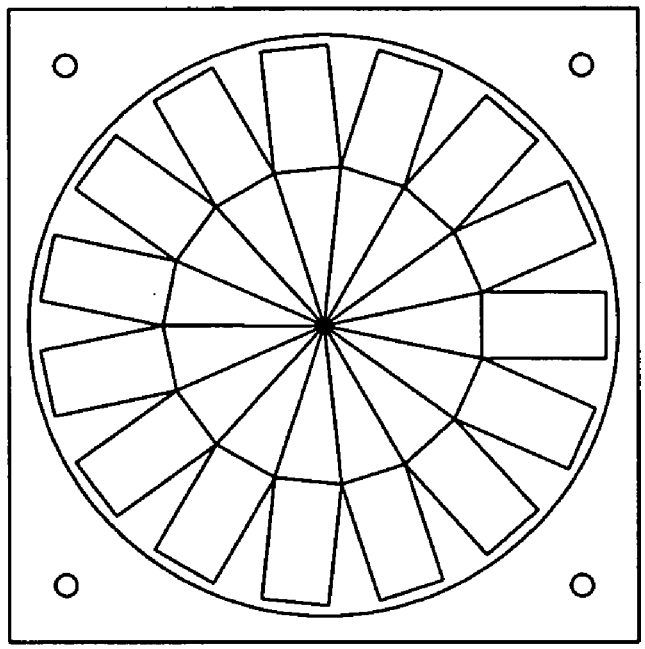
FIG. 11b is a front view of the PRIOR ART crimping device of FIG. 10 with the iris shown in the closed state.
Figure 11A:
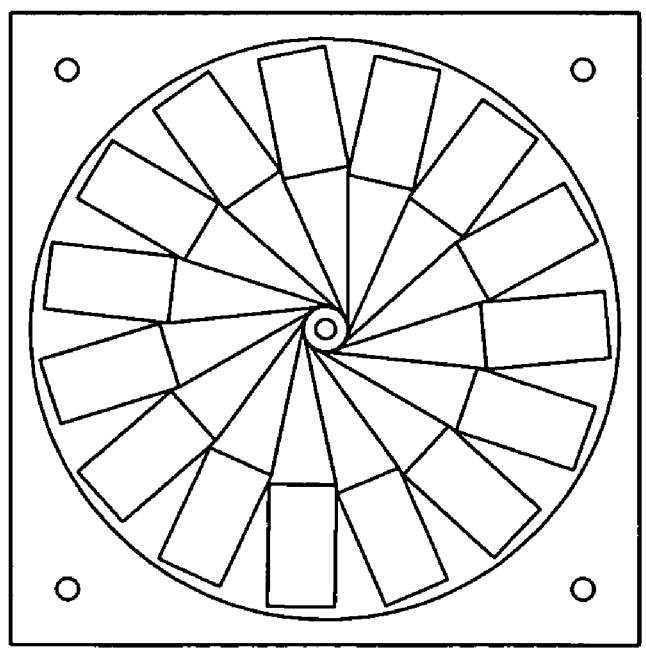
FIG. 11a is a front view of a PRIOR ART crimping device with the iris shown in the open state.

Upon viewing the assembly 100, as depicted in FIG. 2, it will be understood that because of the unique assemblage of components and particularly due to the position of the secondary guidewire housing 104 on the sheath 102 and under the stent 120 to form secondary opening 130a, the assembly 100 is provided with a unique shape which will prevent the stent 120 from being crimped or reduced onto the sheath 102 using a PRIOR ART stent crimper such as is shown in FIGS. 11a and 11b. Crimping devices, such as are describe in U.S. Pat. No. 6,568,235 and U.S. Pat. No. 6,629,350 are equipped with crimping blades which define a variable diameter iris or diameter reduction chamber. The iris however has a constant shape as the blades are configured to apply a uniform radially inward force against the stent in order to crimp or reduce the diameter of the stent in a uniform manner. Because of the different profiles that different regions of the assembly 100 has, such as is illustrated in FIGS. 10a and 10b, it is clear that such a uniform reduction in diameter overall the stent would be detrimental to maintaining the performance characteristics of the assembly 100.

The inability of current crimping systems to crimp the stent 120 and/or assembly 100 may be exacerbated by the need to minimize distortion of the inner diameter of the sheath 102 in order to ensure its ability to freely rotate about a catheter shaft.

As shown in FIG. 10a, the rotatable assembly 100, will have a somewhat eccentric cross-sectional shape at a first region 500, corresponding to where the secondary guidewire housing 104 overlaps the sheath 102 and underlies and 'uplifts' a portion of the stent 120 to form the secondary opening 130a. A second region 502 of the assembly 100, such as is shown in FIG. 10b, which is distal of the distal end of the secondary guidewire housing 104, will have a more traditional, more circular cross-sectional shape. While it may be possible to use the an existing crimping device to crimp the second region 502 of the assembly 100, the eccentric shape of the first region 500 prohibits the use of such a PRIOR ART crimper on the assembly 100 as a whole.

Figure 12:
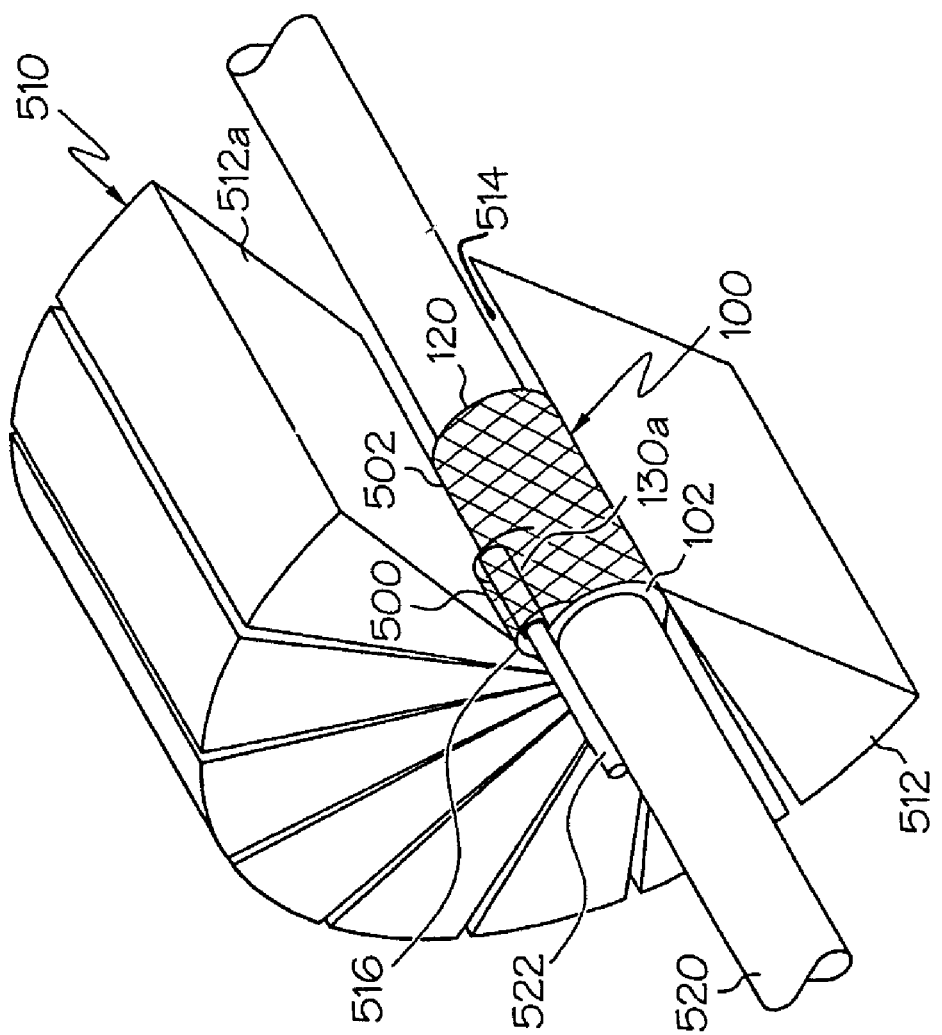
FIG. 12 is a partial cut away view of an embodiment of the invention comprising a crimping apparatus for reducing/crimping the assembly shown in FIG. 2.
Figure 14:
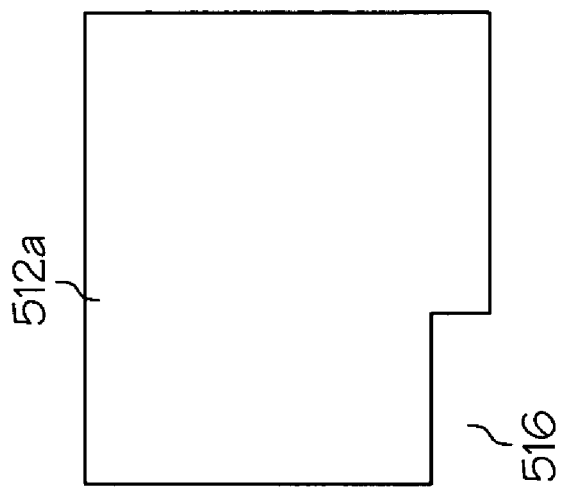
FIG. 14 is a cross-sectional side view of the crimping apparatus shown in FIGS. 12–13.
Figure 13:
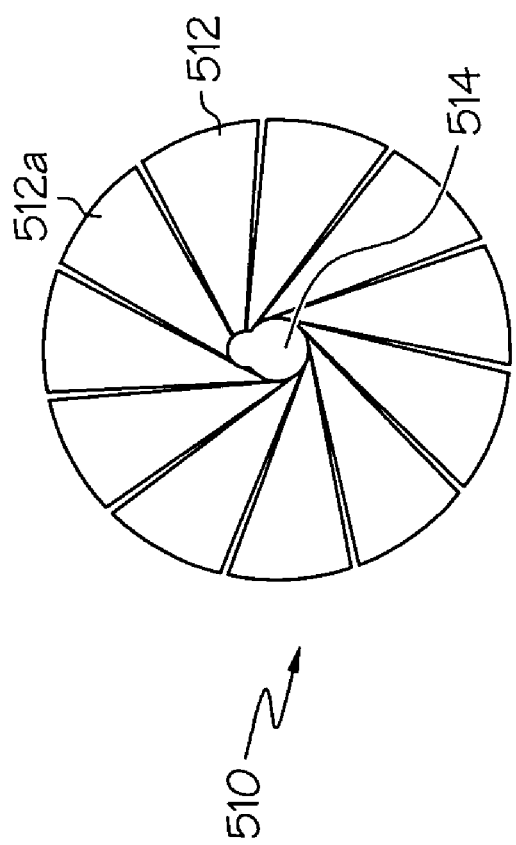
FIG. 13 is a front view of the embodiment shown in FIG. 12, wherein the iris of the crimping apparatus is shown in the open state.

In order to crimp the stent 120 on to the sheath 102 the present invention is directed to several embodiments, which include a unique crimping head 510, such as is depicted in FIGS. 12–14.

The crimping head 510 shown in FIGS. 12–14 is provided with a plurality of moveable blades 512 which define a variable diameter iris 514. The iris 514 is moved between an open position and a closed position by movement of the blades 512. The blades 512 may be moved or engaged to move within the crimping head 510 in any manner desired, including in a manner different or similar to that described in U.S. Pat. No. 6,568,235, U.S. Pat. No. 6,629,350, and/or other references. To accommodate the unique shape of the assembly 100, one or more blades 512 is provided with a stepped shape area 516, or a portion of one or more blades 512 is removed to provide the blade(s) with the stepped shape area 516 desired.

In at least one embodiment the stepped-shape area 516 comprises a soft material, relative to the adjacent portions of the blade, such as for example rubber or silicon, which is able to deform during the crimping process.

Where the area 516 is a groove or space the area 516 defined by the modified blade or blades 512a, is sized and shaped to allow the first region 500 of the assembly to be enclosed therein, such that when the second region 502 is engaged by the blades 512 when the iris 514 is closed, the first region 500 is also engaged with the same degree of force and only minimal or no distortion to the sheath 102 and/or the secondary guidewire housing 104.

The space 516 may be of any length and height, and is limited only by the dimensions of the first region 500 of the assembly 100 and the necessity to apply a force sufficient to reduce the first region 500 of the assembly to the same or similar degree as the second region 502.

In order to ensure that the assembly 100 is not distorted by the crimping process one or more mandrels are used to support the assembly internally. For example in the embodiment shown in FIG. 12, the sheath 102 is disposed on a primary mandrel 520. The primary mandrel resists the radially compressive force of the crimping blades 512 thereby ensuring that the inner diameter of the sheath 102 is maintained. Similarly, a secondary mandrel 522 may be passed through the secondary opening 130a of the stent 120 alone, or within the secondary guidewire housing (not shown).

When used without the secondary guide wire housing the secondary opening 130a of the stent 120 may be maintained and/or formed during the crimping process which allows the secondary guidewire housing to be passed through the secondary opening and/or engaged to the sheath 102 after the fact. If the secondary guide wire housing 104 is already in place in the assembly 100 prior to crimping, such as in the manner depicted in FIG. 2, the secondary mandrel may be passed therethrough in order to prevent the secondary guidewire lumen 106 from being collapsed or distorted during crimping.

Figure 16:
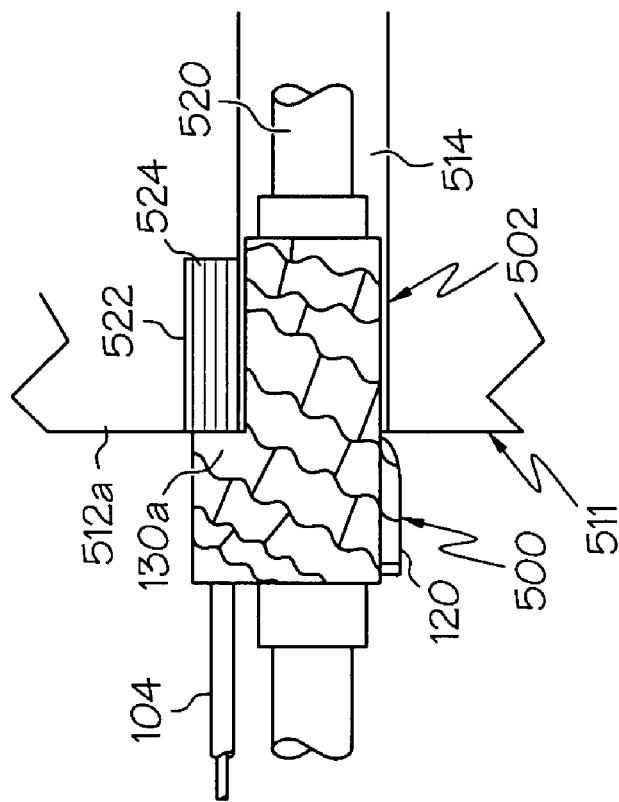
FIG. 16 is a cross-sectional side view of the crimping head shown in FIG. 15 in which the distal portion of the rotatable assembly of FIG. 2 is reduced/crimped.
Figure 15:
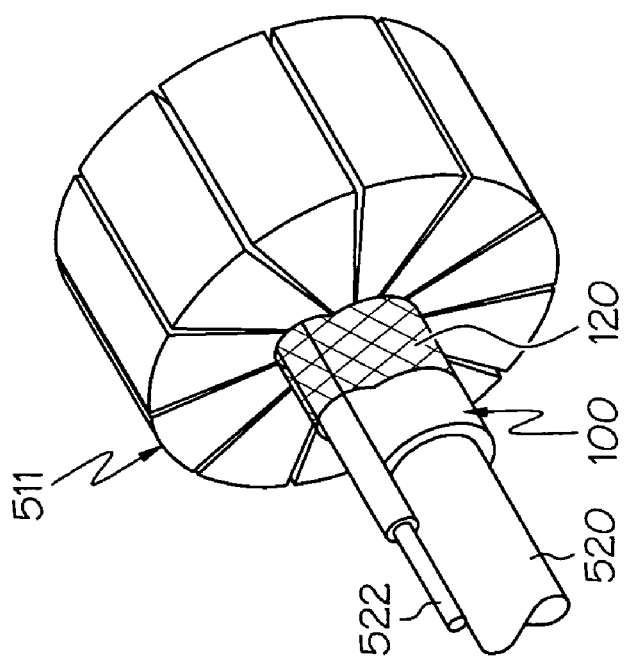
FIG. 15 is a perspective view of an embodiment of the invention comprising a crimping head for reducing\crimping the distal portion of the rotatable assembly of FIG. 2.

In some embodiments, a crimping system may be employed, which requires that the second region 502 of the assembly 100 to be crimped to a desired reduced diameter configuration prior to crimping of the first region 500 of the assembly. In order to accomplish such a two stage crimping process, the assembly 100 is partially inserted into the iris of a first crimping head 511, such as is depicted in FIG. 15, so that the entire assembly 100, distal of the secondary opening 130a of the stent 120, is positioned within the iris 514 such as in the manner shown in FIG. 16. In some embodiments, a blade 512a may be modified to define an opening 524, such as is shown in FIGS. 16 and 17, for the secondary guidewire lumen 104 and/or a secondary mandrel 522 to pass. When the secondary guidewire lumen 104 and/or secondary mandrel 522 is positioned within the opening 524 of the modified blade 512a the secondary guidewire lumen 104 and/or secondary mandrel 522 are not subjected to radially compressive forces when the second region 502 is crimped.

Once the second region 502 has been crimped to a desired diameter, the assembly is removed from the first crimping head 511 and inserted fully into the iris 514 of a second crimping head 513 such as in the manner shown in FIGS. 18 and 19. The second crimping head may have blades 512 which define an iris 514 which has an eccentric or ellipsoid shape, as depicted in FIG. 17. When the blades 512 are moved to reduce the iris 514 to crimp the assembly 100, compressive force is applied substantially to the first region 500 of the assembly 100 as a result of its inherent greater diameter than that of the crimped second region 502. Following crimping of the first region 502, the assembly is removed from the crimping head 513 and is ready for placement on a catheter after removal of the mandrels.

As with the single stage crimping method and apparatus shown in FIGS. 12–14, some embodiments of the two stage crimping method and apparatus shown in FIGS. 15–19 may utilize one or both of a primary mandrel 520 and secondary mandrel 522 to support the respective portions of the assembly 100 and prevent distortion thereof.

The mandrels 520 and 522 respectively, may be provided with a unique construction which may provide additional support to the respective portions of the assembly 100 disposed thereabout, and which may aid in removing the assembly 100 from the mandrels following the crimping process. In the case of the secondary mandrel 522, the secondary mandrel may be configured to form and/or maintain the secondary opening 130a of the stent 120 during the crimping process.

Figure 20:
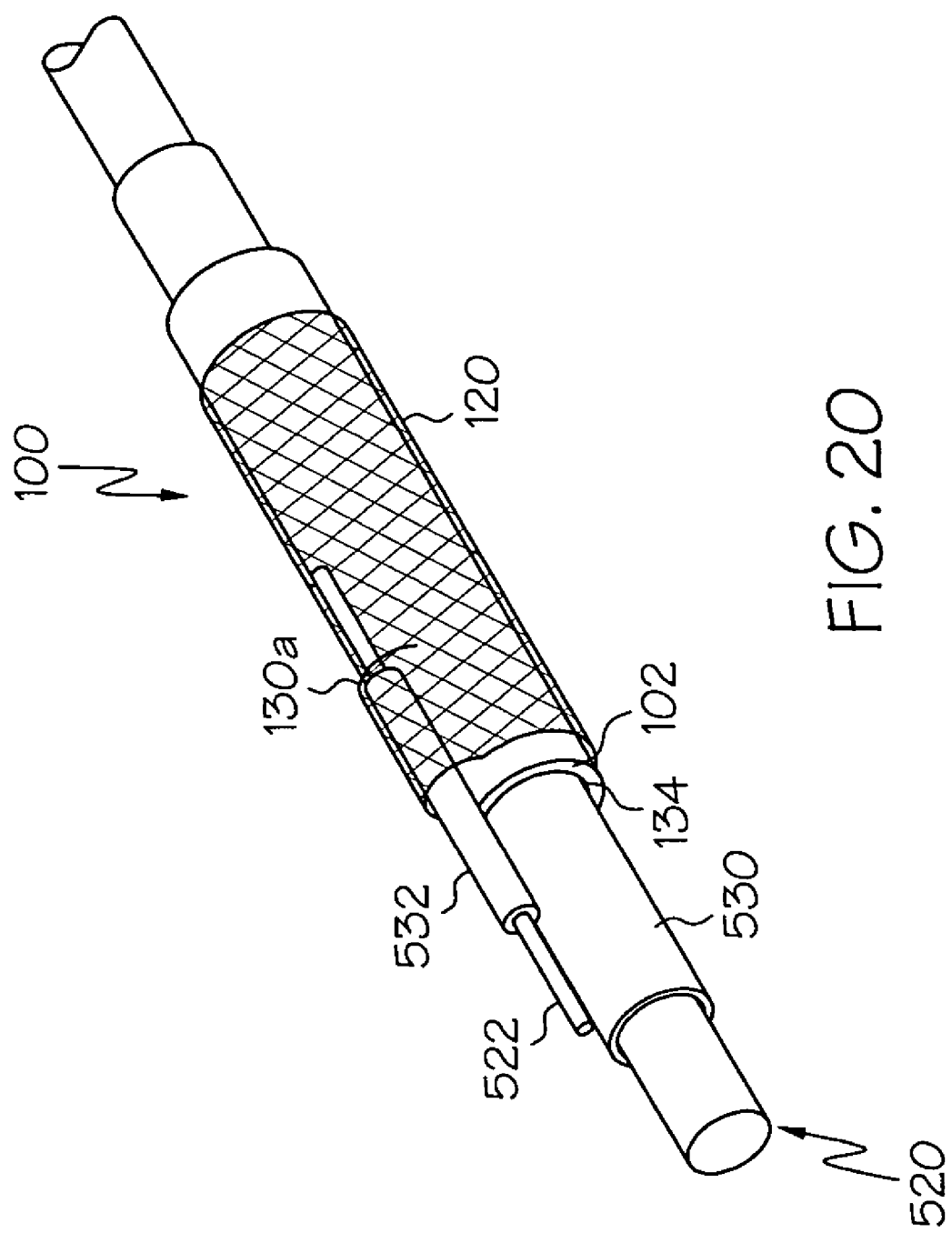
FIG. 20 is a perspective view of an embodiment of the invention comprising an expandable support mandrel and the rotatable assembly of FIG. 2 mounted thereon.

In a first configuration depicted in FIG. 20, one or both mandrels 520 and 522 may be provided with a radially expandable portion 530 and 532 respectively. In the case of the primary mandrel 520, the expandable portion 530 corresponds to at least the length of the sheath 102 which is disposed thereabout. In the case of the secondary mandrel 522, the expandable portion 532 underlies the portion of the stent extending at least from the proximal opening 134 to the secondary opening 130a. In some embodiments a secondary guidewire housing (not shown) may be disposed about the expandable portion 532 prior to or after expansion of the expandable portion 532.

The expandable portions 530 and 532 of the respective mandrels 520 and 522 may have a variety of constructions and configurations. For example in one embodiment, one or both of the expandable portions 530 and 532 may be comprised of a balloon or other expandable member which may be expanded to any diameter desired and which has sufficient structural integrity and strength such that when inflated the balloon will resist deformation caused by the crimping process and/or which may be inflated following crimping to correct any deformation caused by the crimping process.

In another embodiment one or both of the expandable portions 530 and 532 may be comprised of an Electro-Active Polymer (EAP) such as polypyrrole, polyalanine polyacetylene, polythiophene and polyvinylidene difluoride (PVDF), etc. In some embodiments a layer of "Bucky Paper" (a structure of carbon nanotubes) may supplement or replace the EAP. When the EAP is provided with an electric current, the EAP will expand from is nominal state to a predetermined expanded state. The degree of expansion from nominal state to expanded state may be from about a 1% increase in diameter to about 300% increase in diameter, such as in the case of bucky paper.

In at least one embodiment such as is depicted in FIG. 27, either or both mandrels 520 and 522 may be have a multi-layer construction to provide the mandrel, or a portion(s) thereof with the desired expansion characteristics described above. In FIG. 27 a first layer 540 is a conductive layer comprising a conductive wire constructed from: platinum, copper, steel, etc., with single wall carbon nanotubes (SWNT)s filing, etc. A second layer 542 is a proton exchange layer comprising a proton exchange membrane, such as: Nafion, porous Polytetrafluoroethylene (PTFE), porous poly-vinyl octanal acetal (PVO), poly-styrene-isobutylene-styrene (SIBS). A third layer 546 is a carbon nanotube layer comprising bucky paper. A fourth layer 548 is an elastic membrane layer comprising an elastic membrane such as TECHOTHANE® or other similar polyurethane.

Figure 22:
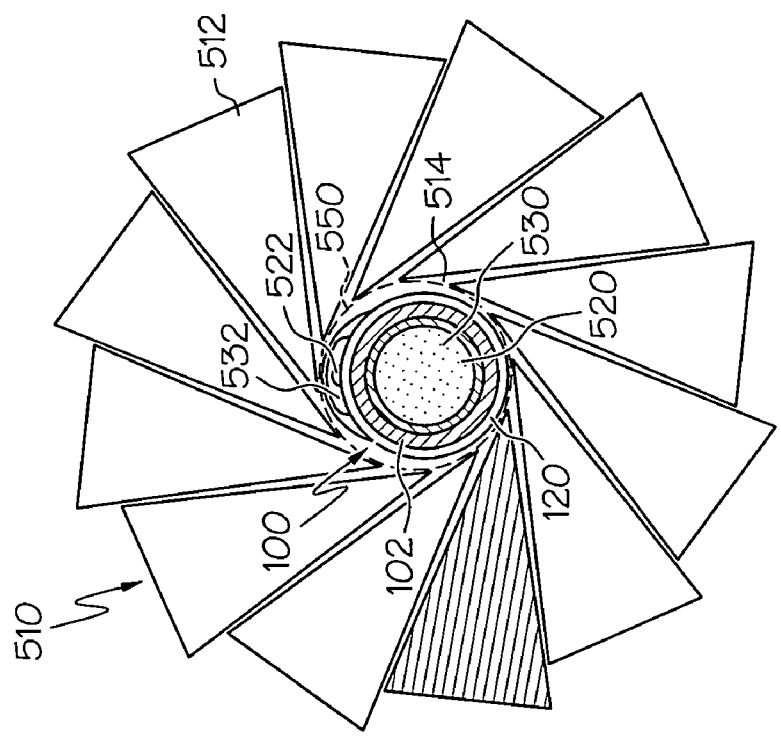
FIG. 22 is a cross-sectional view of the embodiment shown in FIG. 22 wherein the iris of the crimping head is shown in the closed state.
Figure 21:
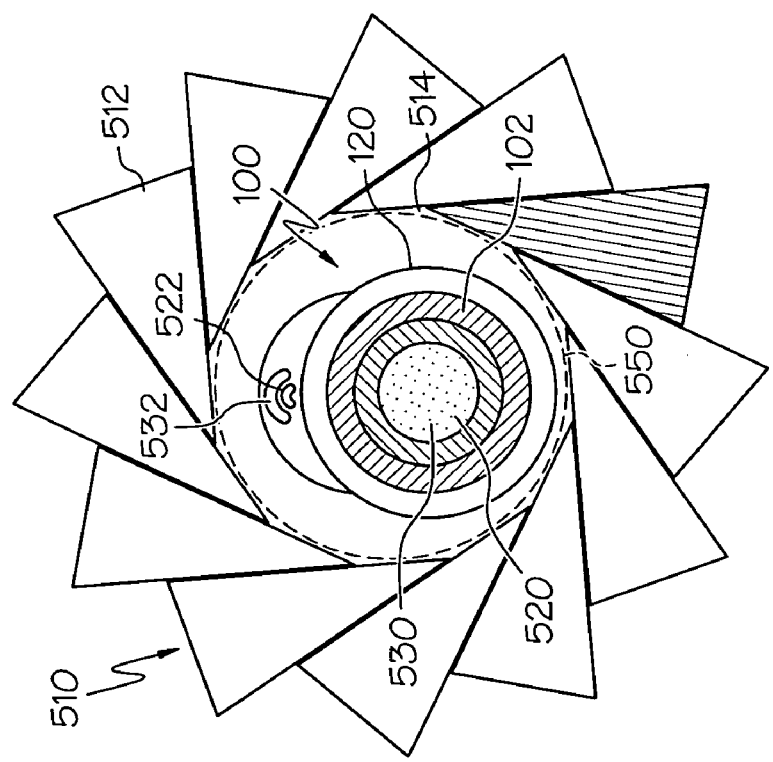
FIG. 21 is a cross-sectional view of the embodiment of the invention shown in FIG. 20 as utilized with a crimping head during a crimping/reducing process, wherein the crimping head is depicted with the iris in the open state.
Figure 28:
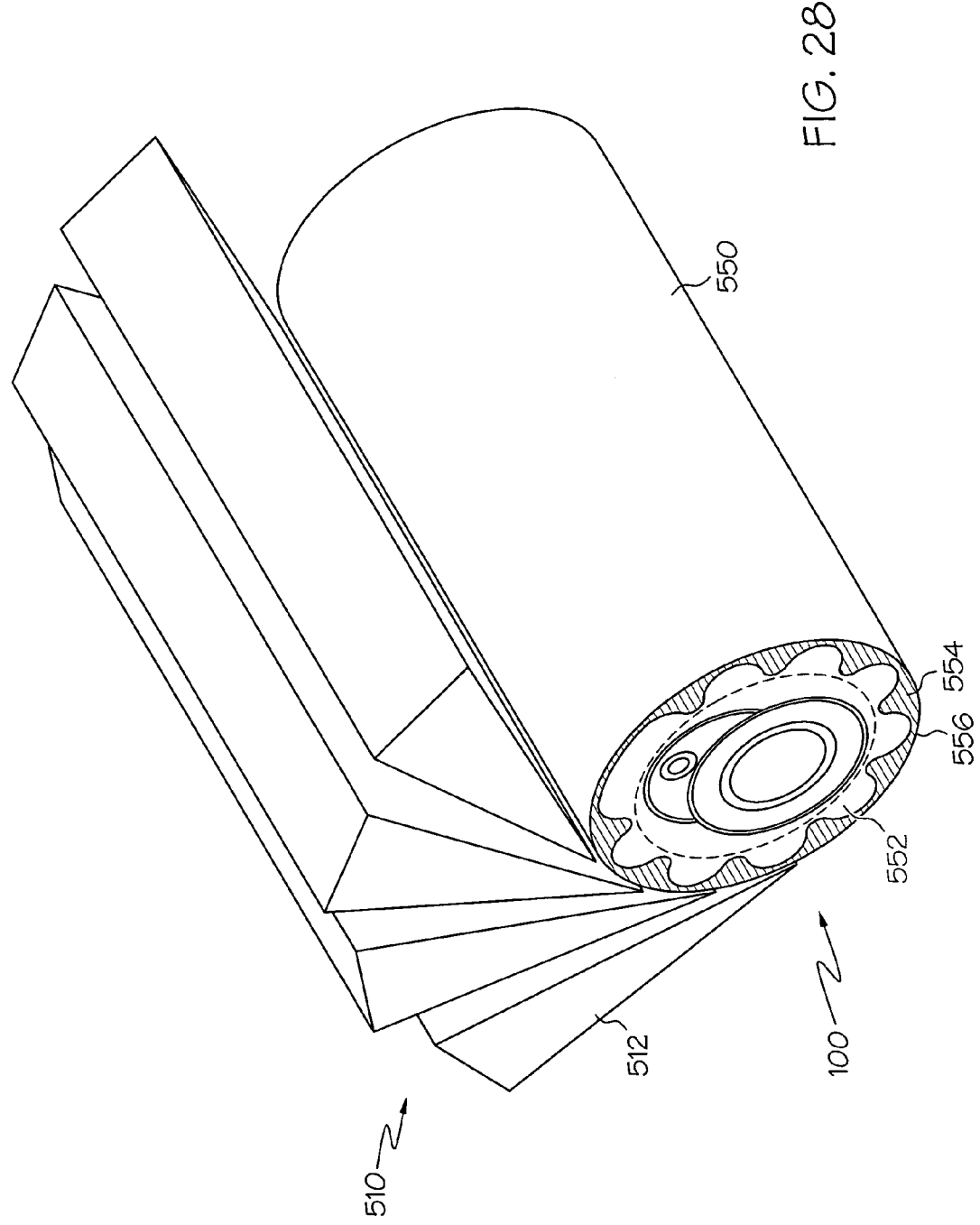
FIG. 28 is a perspective, partial cut-away view of an embodiment of the invention wherein the rotatable assembly of FIG. 2 is provided with a protective crimping sheath for use during reduction/crimping.

The mandrels 520 and 522 protect the assembly 100 from distortion and/or collapse during crimping as illustrated in FIGS. 21 and 22, wherein the assembly 100 is shown within a crimping head 510 wherein the iris 514, in FIG. 21, is in the open state and then in the closed state, in FIG. 22. However it is following the crimping of the assembly 100 where the expandable portions 530 and 532 are particularly useful.

As shown in FIG. 22, when the assembly 100 is fully crimped the secondary opening of the stent 120 may have collapsed or been distorted as a result of the crimping process. As is illustrated in FIG. 23, after removal of the assembly 100 from the crimper, the expandable portion 532 of the secondary mandrel 522 may be expanded. Expansion of the expandable portion 532 of the secondary mandrel 522 has the affect of applying a radially outward acting force, indicated by arrows 534, against the region of the stent 120 extending from the proximal opening 134 to the secondary opening 130a (openings 134 and 13a are shown in FIG. 20). As a result the secondary opening 130a is maintained and/or fully formed by expansion of the secondary mandrel 522 in the manner shown in FIGS. 23 and 24.

In embodiments where the secondary mandrel 522 is passed through the secondary guidewire housing, the expansion of the expandable portion 532 may aid in forming the secondary opening 130a of the stent 120, but also in offsetting any detrimental effects that the inward acting radial force of the crimping blades may have had on the secondary guidewire housing 104. Depending on the degree and timing of the expansion of the expandable portion 532, the secondary guide wire housing may be supported internally, to substantially resist deformation during the crimping process, and/or be expanded to a sufficient extent to allow the mandrel 522 to be readily removed from the secondary guide wire housing following the crimping process.

The amount of force 534 applied by the expandable portion 532 of the secondary mandrel 522 may be varied depending on the extent to which the expandable portion is expanded. In some embodiments the expandable portion 532 is expanded only enough to offset or compensate for the inward application of force applied by the blades of the crimping head and/or the expandable portion 532 by be expanded following the crimping process in order to provide sufficient space to position the secondary guidewire housing 104 between the stent 120 and the sheath 102.

In some embodiments the expandable portion 532 may be expanded to form the secondary opening in the stent following the crimping process and/or return or maintain the secondary guidewire lumen 106 to its pre-crimped diameter, as illustrated in FIG. 24.

As indicated above, in some embodiments the primary mandrel 520 may also employ an expandable portion 522 that underlies the sheath 102 during crimping of the assembly 100. Following or during the crimping process the expandable portion 530 may be expanded to exert a radially outward acting force, indicated by arrows 536. The force 536 may offset or compensate for the radially acting inward force exerted by the crimping blades during the crimping process.

By offsetting the radially inward force of the crimper, during the crimping process, the stent 120 is seated onto the sheath 102 by the opposing forces of the blades and the expandable portion 530. At the same time however, the outward acting force of the expandable portion 530 ensures that the inside diameter remains substantially constant during the crimping process, or alternatively is returned to its original pre-crimped diameter following the crimping process.

In some cases the expandable portion 530 is expanded, and subsequently reduced, following crimping to expand the assembly 100 to a sufficient extent to be able to readily remove the mandrel 520 therefrom, such as is indicated in FIGS. 25 and 26. Once the primary mandrel 520 and secondary mandrel 522 are fully removed from the crimped assembly 100, the assembly is ready for loading onto the catheter 116, such as is in the manner depicted in FIGS. 3 and 4.

As shown in FIGS. 21 and 22, in some embodiments a protective crimping sheath 550 may be disposed about the assembly 100 during the crimping process. The crimping sheath 550 may be especially useful in protecting the external surface of the stent 120 from direct contact with the blades 512 of the crimping head 510. The desire to protect the stent 120 from contact with the blades 512 may be heightened when the stent is provided with a therapeutic coating as described above. In addition to protecting the stent 120, the protective sheath 550 may also be configured to direct the inward acting force applied by the blades 512 to specific areas of the stent 120 and assembly 100.

In order to accomplish such directing of the crimping force, the protective sheath 550, such as is depicted in FIGS. 28–31, may be provided on its inside surface 552 with one or more ridges, bumps, longitudinal insert segments or other raised features 554, which define an undulating or wave pattern of alternating thicker portions 554 and thinner portions 556 in the thickness of the sheath 550. The result is that while the blades 512 of the crimping head 510 exert a variable inward force to the protective sheath 550, the sheath 550 transmits the force to the assembly 100 to those areas 554 which are in contact with the assembly 100.

In some embodiments the inside surface 552 of the protective sheath 550 is provided with one or more coatings of a drug or other therapeutic agent as previously described, such that when the assembly is crimped the crimping force acts in effect like a pad printer placing the therapeutic agent on to the stent during the crimping process.

Figure 29:
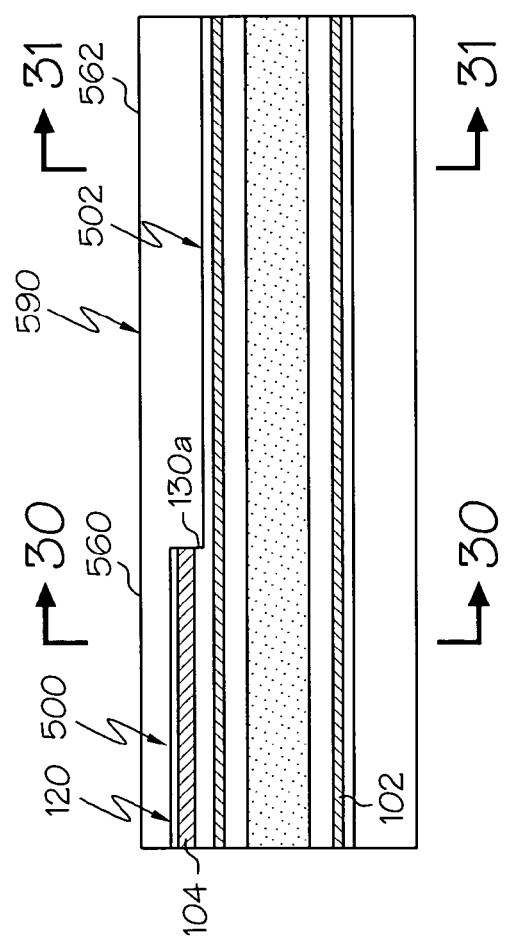
FIG. 29 is a cross-sectional side view of the sheath and assembly shown in FIG. 28.
Figure 31:
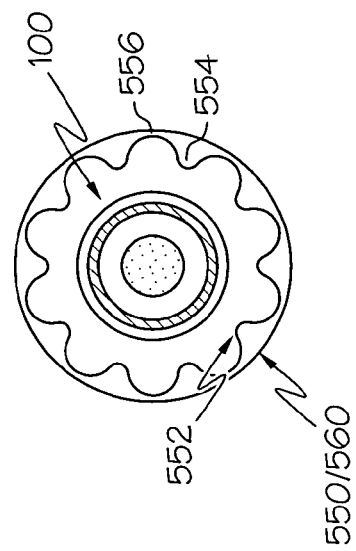
FIG. 31 is a cross-sectional front view of the sheath and rotatable assembly corresponding to section line 'B' in FIG. 29.
Figure 30:
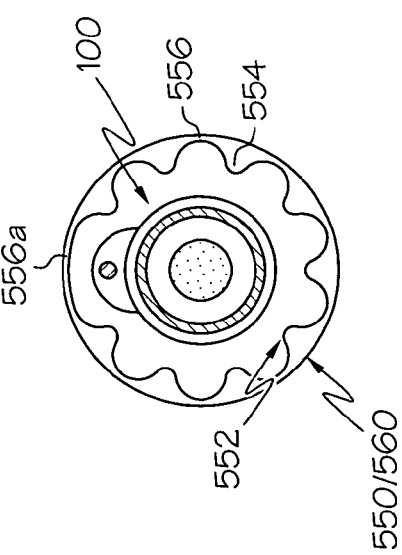
FIG. 30 is a cross-sectional front view of the sheath and rotatable assembly corresponding to section line 'A' in FIG. 29.

Additionally, in some embodiments, an example of which is depicted in FIGS. 29–31 a proximal portion 560 and distal portion 562 of the sheath 550 are provided with differing wave patterns, such that in the pattern in the proximal portion 560 is interrupted by the absence of one or more thicker portions 554 to define a 'longer' thinner portion 556a which has a greater circumferential length than the other thinner portions 556 of the sheath 550. The longer thinner portion 556a overlays the first region 500 of the assembly 100 in the region of the assembly 100 corresponding to the secondary opening 130a of the stent 120 and/or the position of the secondary guidewire housing 104. As a result when the assembly 100 and sheath 550 are crimped, the sheath 550 will tend to transmit the crimping force to the assembly in a non-uniform manner preventing the region of the assembly 100, corresponding to the secondary opening 130a and/or the position of the secondary guidewire housing 104, from being reduced or crimped to the same extend as the rest of the assembly 100.

The sheath 550 may be constructed of any of a variety of polymer materials such as PEBAX, extruded urethane(s), etc.

The invention has been described with reference to the embodiments. Obviously, modifications and alterations will occur to others upon a reading and understanding of this specification. For example, the illustrated embodiments use a balloon to expand the stent although, as briefly noted above, a self expanding, self deploying or hybrid expandable stent can be used without departing from the features of the present invention. The invention is intended to include all such modifications and alterations thereof.

Furthermore, it is noted that the various embodiments shown and described in U.S. patent application Ser. No. 10/375,689, filed Feb. 27, 2003 and U.S. patent application Ser. No. 10/657,472, filed Sep. 8, 2003 both of which are entitled Rotating Balloon Expandable Sheath Bifurcation Delivery; U.S. patent application Ser. No. 10/747,546, filed Dec. 29, 2003 and entitled Rotating Balloon Expandable Sheath Bifurcation Delivery System; and U.S. patent application Ser. No. 10/757,646, filed Jan. 13, 2004 and entitled Bifurcated Stent Delivery System may be incorporated and/or utilized with the various embodiments described herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

With this description, those skilled in the art may recognize other equivalents to the specific embodiment described herein. Such equivalents are intended to be encompassed by the claims attached hereto.

The invention claimed is:

1. A system for reducing the cross-sectional surface area of a stent assembly comprising:
   a stent contracting assembly, the stent contracting assembly comprising a plurality of moveable contracting members, each of the contracting members having a predetermined shape, at least one of the contracting members having a different predetermined shape than the predetermined shape of each of the other contracting members, the plurality of contracting members defining a cross-sectional surface area reduction chamber, the chamber having a reduced cross-sectional surface area configuration and a pre-reduction cross-sectional surface area configuration, the contracting assembly constructed and arranged to receive at least a portion of a stent assembly into the chamber, wherein when the chamber is in the pre-reduction cross-sectional surface area configuration the at least a portion of the stent assembly has a first cross-sectional surface area and when the chamber is in the reduced cross-sectional surface area configuration the at least a portion of the stent assembly has a second cross-sectional surface area, the second cross-sectional surface area being less than the first cross-sectional surface area; and
   a first mandrel, a portion of the first mandrel constructed and arranged to be positioned within the cross-sectional surface area reduction chamber, a first portion of the stent assembly disposed about the portion of the first mandrel;
   a second mandrel, a portion of the second mandrel constructed and arranged to be positioned within the cross-sectional surface area reduction chamber, a second portion of the stent assembly disposed about the portion of the second mandrel.

2. The system of claim 1 wherein the predetermined shape of the contracting members is substantially rectangular.

3. The system of claim 2 wherein a stent assembly engagement surface of the at least one of the contracting members defines a stair-step area.

4. The system of claim 2 wherein a stent assembly engagement surface of the at least one of the contracting members comprises a soft contacting region and a hard contacting region along an axis of the chamber.

5. The system of claim 1 wherein the portion of the first mandrel is expandable from an unexpanded first mandrel diameter to an expanded first mandrel diameter, the expanded first mandrel diameter being greater than the unexpanded first mandrel diameter.

6. The system of claim 5 wherein when the cross-sectional surface area reducing chamber is in the reduced cross-sectional surface area configuration, the first mandrel is positioned within the cross-sectional surface area reducing chamber and the portion of the first mandrel is expanded to the expanded first mandrel diameter.

7. The system of claim 5 wherein when the stent assembly is in the second cross-sectional surface area, the portion of the first mandrel is expanded to the expanded first mandrel diameter.

8. The system of claim 5 wherein the portion of the first mandrel comprises an expandable balloon.

9. The system of claim 5 wherein at least the portion of the first mandrel is at least partially constructed from an electro-active polymer.

10. The system of claim 5 wherein at least the portion of the first mandrel is constructed from one or more layers of the group of layers consisting of: a conductive layer, a proton exchange layer, a carbon nanotube layer, an elastic layer, and any combination thereof.

11. The system of claim 1 wherein the portion of the second mandrel is expandable from an unexpanded second mandrel diameter to an expanded second mandrel diameter, the expanded second mandrel diameter being greater than the unexpanded second mandrel diameter.

12. The system of claim 11 wherein when the cross-sectional surface area reducing chamber is in the reduced cross-sectional surface area configuration, the second mandrel is positioned within the cross-sectional surface area reducing chamber and the portion of the second mandrel is expanded to the expanded second mandrel diameter.

13. The system of claim 11 wherein when the stent assembly is in the second cross-sectional surface area, the portion of the second mandrel is expanded to the expanded second mandrel diameter.

14. The system of claim 5 wherein at least the portion of the first mandrel is constructed from a plurality of layers, the plurality of layers comprising: a conductive layer, a proton exchange layer, a carbon nanotube layer and an elastic membrane layer.

15. The system of claim 11 wherein the portion of the second mandrel comprises an expandable balloon.

16. The system of claim 11 wherein at least the portion of the second mandrel is at least partially constructed from an electro-active polymer.

17. The system of claim 11 wherein at least the portion of the second mandrel is constructed from one or more layers of the group of layers consisting of: a conductive layer, a proton exchange layer, a carbon nanotube layer, an elastic layer, and any combination thereof.

18. The system of claim 11 wherein at least the portion of the second mandrel is constructed from a plurality of layers, the plurality of layers comprising: a conductive layer, a proton exchange layer, a carbon nanotube layer and an elastic membrane layer.

19. The system of claim 1 further comprising a second stent contracting assembly, the second stent contracting assembly comprising a plurality of moveable contracting members, the plurality of contracting members of the second stent contracting assembly defining a cross-sectional surface area reduction chamber of the second stent contracting assembly, the chamber of the second stent contracting assembly having a reduced cross-sectional surface area configuration and a pre-reduction cross-sectional surface area configuration, the second stent contracting assembly constructed and arranged to receive the stent assembly into the chamber, wherein when the chamber of the second stent contracting assembly is in the pre-reduction cross-sectional surface area configuration, a proximal portion of the stent assembly has a first cross-sectional surface area and when the chamber of the second stent contracting assembly is in the reduced cross-sectional surface area configuration, the proximal portion of the stent assembly has a second cross-sectional surface area, the second cross-sectional surface area being less than the first cross-sectional surface area.

20. The system of claim 19 wherein when the chamber of the second stent contracting assembly is in the pre-reduction cross-sectional surface area configuration or the reduced cross-sectional surface area configuration, the cross-sectional surface area of a distal portion of the stent assembly is substantially the same.

21. A system for reducing the cross-sectional surface area of a stent assembly comprising:
a stent contracting assembly, the stent contracting assembly comprising a plurality of moveable contracting members, each of the contracting members having a predetermined shape, at least one of the contracting members having a different predetermined shape than the predetermined shape of each of the other contracting members, the plurality of contracting members defining a cross-sectional surface area reduction chamber, the chamber having a reduced cross-sectional surface area configuration and a pre-reduction cross-sectional surface area configuration, the contracting assembly constructed and arranged to receive at least a portion of a stent assembly into the chamber, wherein when the chamber is in the pre-reduction cross-sectional surface area configuration the at least a portion of the stent assembly has a first cross-sectional surface area and when the chamber is in the reduced cross-sectional surface area configuration the at least a portion of the stent assembly has a second cross-sectional surface area, the second cross-sectional surface area being less than the first cross-sectional surface area; and
a protective sheath, the protective sheath constructed and arranged to be positioned within the cross-sectional surface area reduction chamber, the protective sheath disposed about the stent assembly;
wherein the protective sheath comprises a wall thickness and an inside surface, the inside surface being defined by a wall thickness pattern, the wall thickness pattern comprising alternating thicker portions of the wall thickness and thinner portions of the wall thickness, the thicker portions extending radially inward toward the stent assembly to a greater extent than the thinner portions, a thinner portion being positioned between each thicker portion.

22. The system of claim 21 wherein the protective sheath further comprises a proximal region and a distal region, the inside surface of the proximal region having a pattern of alternating thicker portions of the wall thickness and thinner portions of the wall thickness that is different than the pattern of the distal region.

23. The system of claim 22 wherein the wall thickness pattern of the proximal region of the inner surface of the protective sheath comprises a thinner portion having a greater circumferential length than each of the other thinner portions.

24. The system of claim 22 wherein the protective sheath is at least partially constructed of urethane.

25. The system of claim 24 wherein the protective sheath is formed by extrusion or injection molding.

26. The system of claim 21 wherein the inside surface of the protective sheath comprises at least one therapeutic agent, the at least one therapeutic agent constructed and arranged to be transferred to the at least a portion of the stent assembly when the chamber is in the reduced cross-sectional surface area configuration.

27. The system of claim 26 wherein the at least one therapeutic agent is at least one non-genetic therapeutic agent selected from at least one member of the group consisting of: anti-thrombogenic agents, heparin, heparin derivatives, urokinase, and PPack (dextrophenylalanine proline arginine chloromethylketone); anti-proliferative agents, enoxaprin, angiopeptin, monoclonal antibodies capable of blocking smooth muscle cell proliferation, hirudin, and acetylsalicylic acid; anti-inflammatory agents, dexamethasone, prednisolone, corticosterone, budesonide, estrogen, sulfasalazine, and mesalamine; antineoplastic/antiproliferative/anti-miotic agents, paclitaxel, 5-fluorouracil, cisplatin, vinblastine, vincristine, epothilones, endostatin, angiostatin and thymidine kinase inhibitors; anesthetic agents, lidocaine, bupivacaine and ropivacaine; anti-coagulants, D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters, growth factor inhibitors, growth factor receptor antagonists, transcriptional activators, and translational promoters, vascular cell growth inhibitors, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin; bifunctional molecules consisting of an antibody and a cytotoxin; cholesterol-lowering agents; vasodilating agents; and agents which interfere with endogenous vascoactive mechanisms, and any combinations thereof.

28. The system of claim 26 wherein the at least one therapeutic agent is at least one genetic therapeutic agent selected from at least one member of the group consisting of: anti-sense DNA and RNA; DNA coding for anti-sense RNA, tRNA or rRNA to replace defective or deficient endogenous molecules; angiogenic factors including growth factors, acidic and basic fibroblast growth factors, vascular endothelial growth factor, epidermal growth factor, transforming growth factor .alpha. and .beta., platelet-derived endothelial growth factor, platelet-derived growth factor, tumor necrosis factor .alpha., hepatocyte growth factor and insulin like growth factor; cell cycle inhibitors including CD inhibitors, thymidine kinase ("TK") and other agents useful for interfering with cell proliferation; at least one of the family of bone morphogenic proteins ("BMP's"), BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Any of BMP-2, BMP-3, BMP-4, BMP-5, BMP-6 and BMP-7; dimeric proteins, homodimers, heterodimers, or combinations thereof, alone or together with other molecules; molecules capable of inducing an upstream or downstream effect of a BMP, "hedgehog" proteins, or the DNA's encoding them and any combinations thereof.

29. The system of claim 26 wherein the at least one therapeutic agent is at least one type of cellular material selected from at least one member of the group consisting of:

cells of human origin (autologous or allogeneic); cells of non-human origin (xenogeneic) and any combination thereof.

30. The system of claim 29 wherein the cellular material is selected from at least one member of the group consisting of: side population cells; lineage negative cells; lineage negative CD34⁻ cells; lineage negative CD34⁺ cells; lineage negative ⁻cKit⁺ cells; mesenchymal stem cells; cord blood bells; cardiac or other tissue derived stem cells; whole bone marrow; boner marrow mononuclear cells; endothelial progenitor cells; satellite cells; muscle derived cells; go cells; endothelial cells; adult cardiomyocytes; fibroblasts; smooth muscle cells; cultures of mesenchymal stem cells with 5-aza forces differentiation into cardiomyocytes; adult cardiac fibroblasts +5-aza; genetically modified cells; tissue engineered grafts; MyoD scar fibroblasts; Pacing cells; embryonic stem cell clones; embryonic stem cells; fetal or neonatal cells; immunologically masked cells; tissue engineered grafts; genetically modified cells; teratoma derived cells and any combinations thereof.

31. The system of claim 26 wherein the at least one therapeutic agent comprises at least one polymer coating, the at least one coating selected from at least one member of the group consisting of: polycarboxylic acids; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers, EVA; polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; proteins; polypeptides; silicones; siloxane polymers; polylactic acid; polyglycolic acid; polycaprolactone; polyhydroxybutyrate valerate and blends and copolymers thereof; coatings from polymer dispersions, polyurethane dispersions, fibrin, collagen and derivatives thereof; polysaccharides, celluloses, starches, dextrans, alginates and derivatives; hyaluronic acid; squalene emulsions; polyacrylic acid, a copolymer of polylactic acid and polycaprolactone; medical-grade biodegradable materials, PGA-TMC, Tyrosine-Derived Polycarbonates and arylates; polycaprolactone co butyl acrylate and other co polymers; Poly-L-lactic acid blends with DL-Lactic Acid; Poly(lactic acid-co-glycolic acid); polycaprolactone co PLA; polycaprolactone co butyl acrylate and other copolymers; Tyrosine-Derived Polycarbonates and arylate; poly amino acid; polyphosphazenes; polyiminocarbonates; polydimethyltrimethylcarbonates; biodegradable CA/PO₄'s; cyanoacrylate; 50/50 DLPLG; polydioxanone; polypropylene fumarate; polydepsipeptides; macromolecules, chitosan and Hydroxylpropylmethylcellulose; surface erodible material; maleic anhydride copolymers; zinc-calcium phosphate; amorphous polyanhydrides; sugar; carbohydrate; gelatin; biodegradable polymers; and polymers dissolvable in bodily fluids; A block copolymers; B block copolymers and any combinations thereof.

32. A system for reducing the diameter of a stent assembly comprising:
a stent contracting assembly, the stent contracting assembly comprising a plurality of moveable contracting members, the plurality of contracting members defining a diameter reduction chamber, the chamber having a reduced diameter configuration and a pre-reduction diameter configuration, the stent contracting assembly constructed and arranged to receive the stent assembly into the chamber, wherein when the chamber of the stent contracting assembly is in the pre-reduction diameter configuration at least a portion of the stent assembly has a first diameter and when the chamber is in the reduced diameter configuration the at least a portion of the stent assembly has a second diameter, the second diameter being less than the first diameter;
a first mandrel, a portion of the first mandrel constructed and arranged to be positioned within the diameter reduction chamber, a first portion of the stent assembly disposed about the portion of the first mandrel; and
a protective sheath, the protective sheath constructed and arranged to be positioned within the diameter reduction chamber, the protective sheath disposed about the stent assembly, the protective sheath having a wall thickness and an inside surface, the inside surface being defined by a wall thickness pattern, the wall thickness pattern comprising alternating thicker portions of the wall thickness and thinner portions of the wall thickness, the thicker portions extending radially inward toward the stent assembly to a greater extent than the thinner portions, a thinner portion being positioned between each thicker portion.

33. The system of claim 32 further comprising a second mandrel, a portion of the second mandrel constructed and arranged to be positioned within the diameter reduction chamber, a second portion of the stent assembly disposed about the portion of the second mandrel.

34. A system for reducing the cross-sectional surface area of a stent assembly comprising:
a stent contracting assembly, the stent contracting assembly comprising a plurality of moveable contracting members, each of the contracting members having an elongate edge with a predetermined shape, at least one of the contracting members having a different elongate edge predetermined shape than the elongate edge predetermined shape of each of the other contracting members, the elongate edges of the plurality of contracting members defining a contracting chamber, the contracting chamber having a first cross-sectional shape along a portion of a length of the contracting chamber and a second cross-sectional shape along another portion of the length of the contracting chamber, the first cross-sectional shape having a stepped shape area along only a portion of a circumference of the contracting chamber, the contracting assembly constructed and arranged to receive at least a portion of a stent assembly into the chamber.

35. The system of claim 34 wherein the first cross-sectional shape is generally circular and the second cross-sectional shape is generally ellipsoid shaped.

36. The system of claim 34 wherein the elongate edge predetermined shape of the at least one of the contracting members defines a stair-step shape.

37. The system of claim 34 further comprising a first mandrel, a portion of the first mandrel constructed and arranged to be positioned within the reduction chamber, a first portion of the stent assembly disposed about the portion of the first mandrel.

38. The system of claim 37 wherein the portion of the first mandrel is expandable from an unexpanded first mandrel diameter to an expanded first mandrel diameter, the expanded first mandrel diameter being greater than the unexpanded first mandrel diameter.

39. The system of claim 38 further comprising a second mandrel, a portion of the second mandrel constructed and arranged to be positioned within the reduction chamber, a second portion of the stent assembly disposed about the portion of the second mandrel.

40. The system of claim 39 wherein the portion of the second mandrel is expandable from an unexpanded second mandrel diameter to an expanded second mandrel diameter, the expanded second mandrel diameter being greater than the unexpanded second mandrel diameter.

41. The system of claim 39 wherein the portion of the second mandrel comprises an expandable balloon.

42. The system of claim 39 wherein at least the portion of the second mandrel is at least partially constructed from an electro-active polymer.

43. The system of claim 37 wherein the portion of the first mandrel comprises an expandable balloon.

44. The system of claim 37 wherein at least the portion of the first mandrel is at least partially constructed from an electro-active polymer.

45. A system for reducing the cross-sectional surface area of a stent assembly comprising:

a stent contracting assembly, the stent contracting assembly comprising a plurality of moveable contracting members, each of the contracting members having a predetermined shape, at least one of the contracting members having a different predetermined shape than the predetermined shape of each of the other contracting members, the plurality of contracting members defining a cross-sectional surface area reduction chamber, the chamber having a reduced cross-sectional surface area configuration and a pre-reduction cross-sectional surface area configuration, the contracting assembly constructed and arranged to receive at least a portion of a stent assembly into the chamber, wherein when the chamber is in the pre-reduction cross-sectional surface area configuration the at least a portion of the stent assembly has a first cross-sectional surface area and when the chamber is in the reduced cross-sectional surface area configuration the at least a portion of the stent assembly has a second cross-sectional surface area, the second cross-sectional surface area being less than the first cross-sectional surface area;

a first mandrel, a portion of the first mandrel constructed and arranged to be positioned within the cross-sectional surface area reduction chamber, a first portion of the stent assembly disposed about the portion of the first mandrel and a second stent contracting assembly, the second stent contracting assembly comprising a plurality of moveable contracting members, the plurality of contracting members of the second stent contracting assembly defining a cross-sectional surface area reduction chamber of the second stent contracting assembly, the chamber of the second stent contracting assembly having a reduced cross-sectional surface area configuration and a pre-reduction cross-sectional surface area configuration, the second stent contracting assembly constructed and arranged to receive the stent assembly into the chamber, wherein when the chamber of the second stent contracting assembly is in the pre-reduction cross-sectional surface area configuration, a proximal portion of the stent assembly has a first cross-sectional surface area and when the chamber of the second stent contracting assembly is in the reduced cross-sectional surface area configuration, the proximal portion of the stent assembly has a second cross-sectional surface area, the second cross-sectional surface area being less than the first cross-sectional surface area.

46. The system of claim 45 wherein when the chamber of the second stent contracting assembly is in the pre-reduction cross-sectional surface area configuration or the reduced cross-sectional surface area configuration, the cross-sectional surface area of a distal portion of the stent assembly is substantially the same.

* * * * *